US009081879B2

(12) United States Patent
Iliff

(10) Patent No.: US 9,081,879 B2
(45) Date of Patent: Jul. 14, 2015

(54) MATRIX INTERFACE FOR MEDICAL DIAGNOSTIC AND TREATMENT ADVICE SYSTEM AND METHOD

(75) Inventor: Edwin C. Iliff, La Jolla, CA (US)

(73) Assignee: Clinical Decision Support, LLC, Nashville, TN (US)

( * ) Notice: Subject to any disclaimer, the term of this patent is extended or adjusted under 35 U.S.C. 154(b) by 2318 days.

(21) Appl. No.: 11/258,507

(22) Filed: Oct. 24, 2005

(65) Prior Publication Data

US 2006/0135859 A1 Jun. 22, 2006

Related U.S. Application Data

(60) Provisional application No. 60/621,384, filed on Oct. 22, 2004.

(51) Int. Cl.
*A61B 5/00* (2006.01)
*G06F 19/00* (2011.01)
*G06Q 50/22* (2012.01)

(52) U.S. Cl.
CPC .......... *G06F 19/3406* (2013.01); *G06F 19/345* (2013.01); *G06F 19/363* (2013.01); *G06Q 50/22* (2013.01); *G06F 19/322* (2013.01)

(58) Field of Classification Search
CPC ...... A61B 5/0002; A61B 5/72; A61B 5/7264; A61B 5/7465; A61B 5/7275; A63B 2024/0065; G06F 19/3418; G06F 19/3425; G06F 19/3431; G06Q 10/0635
See application file for complete search history.

(56) References Cited

U.S. PATENT DOCUMENTS

| 3,970,996 | A | 7/1976 | Yasaka et al. |
| 4,051,522 | A | 9/1977 | Healy |
| 4,220,160 | A | 9/1980 | Kimball et al. |
| 4,290,114 | A | 9/1981 | Sinay |
| 4,315,309 | A | 2/1982 | Coli |

(Continued)

FOREIGN PATENT DOCUMENTS

| CN | 1291749 A | 4/2001 |
| CN | 1477581 A | 2/2004 |

(Continued)

OTHER PUBLICATIONS

Alexander G., Health Risk Appraisal, Intern Electro J Health Edu., 2000, 3(Special): 122-137.

(Continued)

*Primary Examiner* — William Thomson
*Assistant Examiner* — Shirley Jian
(74) *Attorney, Agent, or Firm* — Suiter Swantz pc llo

(57) ABSTRACT

An automated medical diagnostic system and method are disclosed. In an embodiment of the system and method, a matrix of cells is displayed via a graphical user interface on a computing device, each cell being representative of a patient health item (PHI) associated with a particular disease. A PHI is entered on the display in one of the cells and a differential diagnosis is updated based on the input PHI. The updated differential diagnosis is then displayed to a user. The system includes multiple diagnostic functions that use the matrix for input and output, wherein the diagnostic functions are selectively executed according to each newly input PHI so as to result in the differential diagnosis. In certain embodiments, the input PHIs are stored in a patient medical record. The computing device can operate independently or in a connection with a system server.

22 Claims, 26 Drawing Sheets

(56) References Cited

U.S. PATENT DOCUMENTS

| | | |
|---|---|---|
| 4,337,377 A | 6/1982 | Van Riper et al. |
| 4,428,381 A | 1/1984 | Hepp |
| 4,458,693 A | 7/1984 | Badzinski et al. |
| 4,465,077 A | 8/1984 | Schneider |
| 4,531,527 A | 7/1985 | Reinhold, Jr. et al. |
| 4,606,352 A | 8/1986 | Geddes et al. |
| 4,712,562 A | 12/1987 | Ohayon et al. |
| 4,731,726 A | 3/1988 | Allen, III |
| 4,733,354 A | 3/1988 | Potter et al. |
| 4,770,189 A | 9/1988 | Shyu |
| 4,803,625 A | 2/1989 | Fu et al. |
| 4,825,869 A | 5/1989 | Sasmor et al. |
| 4,838,275 A | 6/1989 | Lee |
| 4,839,822 A | 6/1989 | Dormond et al. |
| 4,858,121 A | 8/1989 | Barber et al. |
| 4,868,763 A | 9/1989 | Masui et al. |
| 4,933,873 A | 6/1990 | Kaufman et al. |
| 4,945,476 A | 7/1990 | Bodick et al. |
| 4,962,491 A | 10/1990 | Schaeffer |
| 4,974,607 A | 12/1990 | Miwa |
| 4,975,840 A | 12/1990 | DeTore et al. |
| 5,012,411 A | 4/1991 | Policastro et al. |
| 5,012,815 A | 5/1991 | Bennett et al. |
| 5,023,785 A | 6/1991 | Adrion et al. |
| 5,030,948 A | 7/1991 | Rush |
| 5,054,493 A | 10/1991 | Cohn et al. |
| 5,084,819 A | 1/1992 | Dewey et al. |
| 5,099,424 A | 3/1992 | Schneiderman |
| 5,113,869 A | 5/1992 | Nappholz et al. |
| 5,193,541 A | 3/1993 | Hatsuwi |
| 5,196,682 A | 3/1993 | Englehardt |
| 5,228,449 A | 7/1993 | Christ et al. |
| 5,235,510 A | 8/1993 | Yamada et al. |
| 5,241,621 A | 8/1993 | Smart |
| 5,255,187 A | 10/1993 | Sorensen |
| 5,257,627 A | 11/1993 | Rapoport |
| 5,263,123 A | 11/1993 | Hayashi |
| 5,265,613 A | 11/1993 | Feldman et al. |
| 5,299,121 A | 3/1994 | Brill et al. |
| 5,307,263 A | 4/1994 | Brown |
| 5,337,752 A | 8/1994 | Reeves |
| 5,347,632 A | 9/1994 | Filepp et al. |
| 5,357,427 A | 10/1994 | Langen et al. |
| 5,377,258 A | 12/1994 | Bro |
| 5,390,238 A | 2/1995 | Kirk et al. |
| 5,404,292 A | 4/1995 | Hendrickson |
| 5,415,167 A | 5/1995 | Wilk |
| 5,418,888 A | 5/1995 | Alden |
| 5,421,343 A | 6/1995 | Feng |
| 5,435,324 A | 7/1995 | Brill |
| 5,437,278 A | 8/1995 | Wilk |
| 5,441,047 A | 8/1995 | David et al. |
| 5,442,728 A | 8/1995 | Kaufman et al. |
| 5,463,548 A | 10/1995 | Asada et al. |
| 5,471,382 A | 11/1995 | Tallman et al. |
| 5,473,537 A | 12/1995 | Glazer et al. |
| 5,481,647 A | 1/1996 | Brody et al. |
| 5,486,999 A | 1/1996 | Mebane |
| 5,517,405 A | 5/1996 | McAndrew et al. |
| 5,519,433 A | 5/1996 | Lappington et al. |
| 5,533,522 A | 7/1996 | Feng |
| 5,541,977 A | 7/1996 | Hodges et al. |
| 5,544,649 A | 8/1996 | David et al. |
| 5,553,609 A | 9/1996 | Chen et al. |
| 5,555,169 A | 9/1996 | Namba et al. |
| 5,572,421 A | 11/1996 | Altman et al. |
| 5,583,758 A | 12/1996 | McIlroy et al. |
| 5,594,638 A | 1/1997 | Iliff |
| 5,596,994 A | 1/1997 | Bro |
| 5,601,435 A | 2/1997 | Quy |
| 5,619,991 A | 4/1997 | Sloane |
| 5,622,171 A | 4/1997 | Asada et al. |
| 5,633,910 A | 5/1997 | Cohen |
| 5,642,731 A | 7/1997 | Kehr |
| 5,642,936 A | 7/1997 | Evans |
| 5,659,793 A | 8/1997 | Escobar et al. |
| 5,660,176 A | 8/1997 | Iliff |
| 5,672,154 A | 9/1997 | Sillén et al. |
| 5,675,760 A | 10/1997 | Houwen et al. |
| 5,678,562 A | 10/1997 | Sellers |
| 5,692,220 A | 11/1997 | Diamond et al. |
| 5,692,501 A | 12/1997 | Minturn |
| 5,694,939 A | 12/1997 | Cowings |
| 5,703,786 A | 12/1997 | Conkright |
| 5,711,297 A | 1/1998 | Iliff |
| 5,722,418 A | 3/1998 | Bro |
| 5,724,968 A | 3/1998 | Iliff |
| 5,724,983 A | 3/1998 | Selker et al. |
| 5,732,397 A | 3/1998 | DeTore et al. |
| 5,746,204 A | 5/1998 | Schauss |
| 5,769,074 A | 6/1998 | Barnhill et al. |
| 5,772,585 A | 6/1998 | Lavin et al. |
| 5,778,882 A | 7/1998 | Raymond et al. |
| 5,788,640 A | 8/1998 | Peters |
| 5,794,208 A | 8/1998 | Goltra |
| 5,800,347 A | 9/1998 | Skates et al. |
| 5,802,495 A | 9/1998 | Goltra |
| 5,812,984 A | 9/1998 | Goltra |
| 5,822,715 A | 10/1998 | Worthington et al. |
| 5,823,949 A | 10/1998 | Goltra |
| 5,828,943 A | 10/1998 | Brown |
| 5,832,448 A | 11/1998 | Brown |
| 5,835,900 A | 11/1998 | Fagg, III et al. |
| 5,839,430 A | 11/1998 | Cama |
| 5,862,304 A | 1/1999 | Ravdin et al. |
| 5,868,669 A | 2/1999 | Iliff |
| 5,879,163 A | 3/1999 | Brown et al. |
| 5,887,133 A | 3/1999 | Brown et al. |
| 5,897,493 A | 4/1999 | Brown |
| 5,899,855 A | 5/1999 | Brown |
| 5,908,383 A | 6/1999 | Brynjestad |
| 5,909,679 A | 6/1999 | Hall |
| 5,910,107 A | 6/1999 | Iliff |
| 5,911,132 A | 6/1999 | Sloane |
| 5,918,603 A | 7/1999 | Brown |
| 5,933,136 A | 8/1999 | Brown |
| 5,935,060 A | 8/1999 | Iliff |
| 5,940,801 A | 8/1999 | Brown |
| 5,951,300 A | 9/1999 | Brown |
| 5,953,704 A | 9/1999 | McIlroy et al. |
| 5,956,501 A | 9/1999 | Brown |
| 5,960,403 A | 9/1999 | Brown |
| 5,974,389 A | 10/1999 | Clark et al. |
| 5,976,082 A | 11/1999 | Wong et al. |
| 5,987,519 A | 11/1999 | Peifer |
| 5,997,476 A | 12/1999 | Brown |
| 6,001,060 A | 12/1999 | Churchill et al. |
| 6,022,315 A | 2/2000 | Iliff |
| 6,032,119 A | 2/2000 | Brown et al. |
| 6,032,678 A * | 3/2000 | Rottem ................. 600/437 |
| 6,071,236 A | 6/2000 | Iliff |
| 6,081,786 A | 6/2000 | Barry et al. |
| 6,101,478 A | 8/2000 | Brown |
| 6,106,459 A | 8/2000 | Clawson |
| 6,113,540 A | 9/2000 | Iliff |
| 6,117,073 A | 9/2000 | Jones et al. |
| 6,144,837 A | 11/2000 | Quy |
| 6,149,585 A | 11/2000 | Gray |
| 6,151,586 A | 11/2000 | Brown |
| 6,161,095 A | 12/2000 | Brown |
| 6,167,362 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| 6,196,970 B1 | 3/2001 | Brown |
| 6,206,829 B1 | 3/2001 | Iliff |
| 6,230,142 B1 | 5/2001 | Benigno et al. |
| 6,233,539 B1 | 5/2001 | Brown |
| 6,234,964 B1 | 5/2001 | Iliff |
| 6,240,393 B1 | 5/2001 | Brown |
| 6,246,975 B1 | 6/2001 | Rivonelli et al. |
| 6,246,992 B1 | 6/2001 | Brown |
| 6,247,002 B1 | 6/2001 | Steels |

(56) References Cited

U.S. PATENT DOCUMENTS

| | | |
|---|---|---|
| 6,248,063 B1 | 6/2001 | Barnhill et al. |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,330,426 B2 | 12/2001 | Brown et al. |
| 6,334,778 B1 | 1/2002 | Brown |
| 6,368,273 B1 | 4/2002 | Brown |
| 6,375,469 B1 | 4/2002 | Brown |
| 6,379,301 B1 | 4/2002 | Worthington et al. |
| 6,381,577 B1 | 4/2002 | Brown |
| 6,383,135 B1 * | 5/2002 | Chikovani et al. ............ 600/300 |
| 6,468,210 B1 | 10/2002 | Iliff |
| 6,475,143 B2 | 11/2002 | Iliff |
| 6,482,156 B2 | 11/2002 | Iliff |
| 6,524,241 B2 | 2/2003 | Iliff |
| 6,527,713 B2 | 3/2003 | Iliff |
| 6,569,093 B2 | 5/2003 | Iliff |
| 6,597,392 B1 | 7/2003 | Jenkins et al. |
| 6,598,035 B2 | 7/2003 | Branson et al. |
| 6,601,055 B1 | 7/2003 | Roberts |
| 6,641,532 B2 | 11/2003 | Iliff |
| 6,687,685 B1 | 2/2004 | Sadeghi et al. |
| 6,725,209 B1 | 4/2004 | Iliff |
| 6,730,027 B2 | 5/2004 | Iliff |
| 6,736,776 B2 * | 5/2004 | Miles ............................ 600/300 |
| 6,746,399 B2 | 6/2004 | Iliff |
| 6,748,353 B1 | 6/2004 | Iliff |
| 6,764,447 B2 | 7/2004 | Iliff |
| 6,767,325 B2 | 7/2004 | Iliff |
| 6,770,029 B2 | 8/2004 | Iliff |
| 6,817,980 B2 | 11/2004 | Iliff |
| 6,849,045 B2 | 2/2005 | Iliff |
| 6,900,807 B1 | 5/2005 | Liongosari et al. |
| 6,903,657 B2 | 6/2005 | Kwoen |
| 6,968,375 B1 | 11/2005 | Brown |
| 7,076,437 B1 | 7/2006 | Levy |
| 7,081,091 B2 * | 7/2006 | Merrett et al. ................. 600/300 |
| 7,149,756 B1 * | 12/2006 | Schmitt et al. ......................... 1/1 |
| 7,167,818 B2 | 1/2007 | Brown |
| 7,223,235 B2 | 5/2007 | Brown |
| 7,223,236 B2 | 5/2007 | Brown |
| 7,252,636 B2 | 8/2007 | Brown |
| 7,258,666 B2 | 8/2007 | Brown |
| 7,259,681 B2 | 8/2007 | Kwoen |
| 7,264,591 B2 | 9/2007 | Brown |
| 7,297,108 B2 | 11/2007 | Iliff |
| 7,297,109 B2 | 11/2007 | Brown |
| 7,297,111 B2 | 11/2007 | Iliff |
| 7,300,402 B2 | 11/2007 | Iliff |
| 7,305,348 B1 | 12/2007 | Brown |
| 7,306,560 B2 | 12/2007 | Iliff |
| 7,310,668 B2 | 12/2007 | Brown |
| 7,320,030 B2 | 1/2008 | Brown |
| 7,344,496 B2 | 3/2008 | Iliff |
| 7,392,167 B2 | 6/2008 | Brown |
| 7,399,276 B1 | 7/2008 | Brown et al. |
| 7,421,140 B2 * | 9/2008 | Rottem ........................ 382/254 |
| 7,516,192 B2 | 4/2009 | Brown |
| 7,698,154 B2 * | 4/2010 | Marchosky ........................ 705/3 |
| 7,769,600 B2 | 8/2010 | Iliff |
| 7,780,595 B2 | 8/2010 | Iliff |
| 7,899,687 B2 * | 3/2011 | Morris ............................... 705/3 |
| 2001/0012913 A1 | 8/2001 | Iliff |
| 2001/0039503 A1 | 11/2001 | Chan et al. |
| 2001/0053875 A1 | 12/2001 | Iliff |
| 2002/0019749 A1 * | 2/2002 | Becker et al. ..................... 705/2 |
| 2002/0029157 A1 * | 3/2002 | Marchosky ........................ 705/3 |
| 2002/0068857 A1 | 6/2002 | Iliff |
| 2002/0148477 A1 | 10/2002 | Kwoen |
| 2002/0170565 A1 * | 11/2002 | Walker et al. ................. 128/920 |
| 2002/0186818 A1 | 12/2002 | Arnaud et al. |
| 2003/0036686 A1 | 2/2003 | Iliff |
| 2003/0069753 A1 | 4/2003 | Brown |
| 2003/0153819 A1 | 8/2003 | Iliff |
| 2003/0163299 A1 | 8/2003 | Iliff |
| 2003/0181790 A1 | 9/2003 | David et al. |
| 2003/0225315 A1 * | 12/2003 | Merrett et al. ................. 600/300 |
| 2004/0017475 A1 | 1/2004 | Akers et al. |
| 2004/0019259 A1 | 1/2004 | Brown |
| 2004/0059200 A1 | 3/2004 | Iliff |
| 2004/0107116 A1 | 6/2004 | Brown |
| 2004/0116780 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0193377 A1 | 9/2004 | Brown |
| 2004/0199332 A1 | 10/2004 | Iliff |
| 2004/0199409 A1 | 10/2004 | Brown |
| 2004/0219500 A1 | 11/2004 | Brown |
| 2004/0249778 A1 | 12/2004 | Iliff |
| 2005/0010088 A1 | 1/2005 | Iliff |
| 2005/0010444 A1 | 1/2005 | Iliff |
| 2005/0027562 A1 | 2/2005 | Brown |
| 2005/0060194 A1 | 3/2005 | Brown |
| 2005/0080652 A1 | 4/2005 | Brown |
| 2005/0086083 A1 | 4/2005 | Brown |
| 2005/0134609 A1 * | 6/2005 | Yu ................... 345/629 |
| 2005/0177391 A1 | 8/2005 | Shimizu et al. |
| 2005/0228883 A1 | 10/2005 | Brown |
| 2005/0234306 A1 | 10/2005 | Schulte et al. |
| 2005/0256739 A1 | 11/2005 | Brown |
| 2005/0273359 A1 | 12/2005 | Young |
| 2005/0273509 A1 | 12/2005 | Brown |
| 2006/0004611 A1 | 1/2006 | Brown |
| 2006/0010014 A1 | 1/2006 | Brown |
| 2006/0089969 A1 | 4/2006 | Brown |
| 2006/0100910 A1 | 5/2006 | Brown |
| 2006/0178914 A1 | 8/2006 | Brown |
| 2006/0189853 A1 | 8/2006 | Brown |
| 2006/0206012 A1 * | 9/2006 | Merrett et al. ................. 600/300 |
| 2006/0234202 A1 | 10/2006 | Brown |
| 2006/0235722 A1 | 10/2006 | Brown |
| 2006/0241975 A1 | 10/2006 | Brown |
| 2006/0247951 A1 | 11/2006 | Brown |
| 2006/0247979 A1 | 11/2006 | Brown |
| 2006/0252089 A1 | 11/2006 | Brown |
| 2006/0253303 A1 | 11/2006 | Brown |
| 2006/0253574 A1 | 11/2006 | Brown |
| 2006/0253576 A1 | 11/2006 | Brown |
| 2006/0271404 A1 | 11/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0294233 A1 | 12/2006 | Brown |
| 2007/0016445 A1 | 1/2007 | Brown |
| 2007/0016446 A1 | 1/2007 | Brown |
| 2007/0016447 A1 | 1/2007 | Brown |
| 2007/0016448 A1 | 1/2007 | Brown |
| 2007/0021984 A1 | 1/2007 | Brown |
| 2007/0048691 A1 | 3/2007 | Brown |
| 2007/0055486 A1 | 3/2007 | Brown |
| 2007/0061167 A1 | 3/2007 | Brown |
| 2007/0067251 A1 | 3/2007 | Brown |
| 2007/0078681 A1 | 4/2007 | Brown |
| 2007/0094049 A1 | 4/2007 | Brown |
| 2007/0100665 A1 | 5/2007 | Brown |
| 2007/0100934 A1 | 5/2007 | Brown |
| 2007/0111176 A1 | 5/2007 | Brown |
| 2007/0118403 A1 | 5/2007 | Brown |
| 2007/0118404 A1 | 5/2007 | Brown |
| 2007/0124179 A1 | 5/2007 | Brown |
| 2007/0168226 A1 | 7/2007 | Brown |
| 2007/0168242 A1 | 7/2007 | Brown |
| 2007/0212671 A1 | 9/2007 | Brown |
| 2007/0213608 A1 | 9/2007 | Brown |
| 2007/0239490 A1 * | 10/2007 | Sullivan ........................... 705/3 |
| 2007/0299321 A1 | 12/2007 | Brown |
| 2008/0004915 A1 | 1/2008 | Brown |
| 2008/0045811 A1 | 2/2008 | Iliff |
| 2008/0046268 A1 | 2/2008 | Brown |
| 2008/0051638 A1 | 2/2008 | Iliff |
| 2008/0051639 A1 | 2/2008 | Iliff |

(56) References Cited

U.S. PATENT DOCUMENTS

| | | |
|---|---|---|
| 2008/0051640 A1 | 2/2008 | Iliff |
| 2008/0051641 A1 | 2/2008 | Iliff |
| 2008/0052116 A1 | 2/2008 | Iliff |
| 2008/0052118 A1 | 2/2008 | Iliff |
| 2008/0052119 A1 | 2/2008 | Iliff |
| 2008/0052120 A1 | 2/2008 | Iliff |
| 2008/0052121 A1 | 2/2008 | Iliff |
| 2008/0052122 A1 | 2/2008 | Iliff |
| 2008/0052123 A1 | 2/2008 | Iliff |
| 2008/0052130 A1 | 2/2008 | Iliff |
| 2008/0052132 A1 | 2/2008 | Iliff |
| 2008/0052318 A1 | 2/2008 | Iliff |
| 2008/0059227 A1 | 3/2008 | Clapp |
| 2008/0059232 A1 | 3/2008 | Iliff |
| 2008/0059247 A1 | 3/2008 | Iliff |
| 2008/0072147 A1 | 3/2008 | Brown |
| 2008/0097180 A1 | 4/2008 | Brown |
| 2008/0097181 A1 | 4/2008 | Brown |
| 2008/0103377 A1 | 5/2008 | Brown |
| 2008/0108888 A1 | 5/2008 | Brown |
| 2008/0109172 A1 | 5/2008 | Brown |
| 2008/0162393 A1 | 7/2008 | Iliff |
| 2008/0262557 A1 | 10/2008 | Brown |
| 2008/0269571 A1 | 10/2008 | Brown |
| 2009/0007924 A1 | 1/2009 | Iliff |

FOREIGN PATENT DOCUMENTS

| | | |
|---|---|---|
| DE | 4430184 C2 | 3/1995 |
| DE | 4430164 A1 | 2/1996 |
| EP | 0 320 749 A2 | 12/1988 |
| EP | 0 447 710 A1 | 9/1991 |
| EP | 0 531 889 A2 | 3/1993 |
| EP | 0 643 360 A2 | 3/1996 |
| EP | 0 720 336 A2 | 7/1996 |
| JP | 03191952 | 8/1991 |
| JP | 3202047 | 9/1991 |
| JP | 04015035 | 1/1992 |
| JP | 04015035 A | 1/1992 |
| JP | 4056561 | 2/1992 |
| JP | 06083847 | 3/1994 |
| JP | 06274472 | 9/1994 |
| JP | 08117210 A | 5/1996 |
| JP | 08140944 | 6/1996 |
| JP | 08164127 A | 6/1996 |
| JP | 08275927 | 10/1996 |
| WO | WO 93/23819 | 11/1993 |
| WO | WO 94/00817 | 1/1994 |
| WO | WO 94/06088 | 3/1994 |
| WO | WO 95/06296 | 3/1995 |
| WO | WO 95/06298 | 3/1995 |
| WO | WO 95/19604 | 7/1995 |
| WO | WO 96/22577 | 7/1996 |
| WO | WO 97/05553 | 2/1997 |
| WO | WO 98/02836 | 1/1998 |
| WO | WO 98/40835 | 9/1998 |
| WO | WO 99/52025 | 10/1999 |
| WO | WO 00/32088 | 6/2000 |
| WO | WO 01/61616 A2 | 8/2001 |
| WO | WO 01/85021 A1 | 11/2001 |
| WO | WO 02/39250 A2 | 5/2002 |
| WO | WO 02/42876 A2 | 5/2002 |
| WO | WO 03/040879 A2 | 5/2003 |
| WO | WO 03/040964 A2 | 5/2003 |
| WO | WO 03/040965 A2 | 5/2003 |
| WO | WO 03/040989 A2 | 5/2003 |
| WO | WO 03/040990 A2 | 5/2003 |

OTHER PUBLICATIONS

Ellis et al., Health Education Using Microcomputers II: One year in the Clinic; Preventive Medicine, 1982, 11: 212-224.
Ellis et al., Health Education using Microcomputers: Initial Acceptability, Preventive Medicine, Jan. 1981, 10(1): 77-84.
Fielding J., Appraising the Health of Health Risk Appraisal, Am J Pub Health, Apr. 1982, 72(4): 337-340.
Goetz et al., Health Risk Appraisal: The Estimation of Risk, Health Promotion at the Worksite, Mar.-Apr. 1980, 95(2): 119-126.
Replacement Statement and Explanation dated Nov. 21, 2009 from Request for Ex Parte Reexamination of U.S. Patent No. 6,116,540; U.S. Appl. No. 90/009594, filed Nov. 21, 2009.
Gale et al., *Medical Diagnosis From Student to Clinician*, p. 1-22 (1983).
Gini et al., "A Serial Model for Computer Assisted Medical Diagnosis," Int. J. Bio-Medical Computing (11) (1980) pp. 99-113.
Office Action for Japanese Patent Application No. 506146/98 (and English language translation).
Applied Medical Informatics, Inc., "Medical House CallTM Interactive Home Medical Guide & Symptom Analysis", Applied Medical Informatics, 1995, pp. 24-Jan., Salt Lake City, UT.
Barnett et al., A computer-based medical information system for ambulatory care, Proc. IEEE, 1979, Issue 67, pp. 1226-1237.
Bouhaddou et al., An interactive patient information and education system (Medical HouseCall) based on a physician expert system (Iliad), Medinfo, 1995, vol. Pt 2, Issue 8, pp. 1181-1185, Vancouver, Canada.
Bouhaddou et al., AMIA, Inc., pp. 742-746, 1995, "Iliad and Medical House Call: evaluating the impact of common sense knowledge on the diagnostic accuracy of a medical expert system".
Collen, Machine diagnosis from a multiphasic screening program, Proceedings of $5^{th}$ IBM Medical Symposium at 131, 1963.
Cope, for well-connected in study, computer's diagnosis is just a phone call away, Minneappolis Star-Tribune, Mar. 1992, pp. 03E.
Crossman, Confused? Take two aspirin and call up advisor, New Jersey Record, Apr. 1992, pp. B02.
Dawson, Sun, Microsoft battle over Net computing, Multichannel News, Nov. 1996.
Gorry et al., Decision analysis as the basis for computer-aided management of acute renal failure, Am. J. Med., Oct. 1973, vol. 3, Issue 55, pp. 473-484.
Lai, Abstraction models at system level for interactive multimedia scripting, Master's Thesis, Massachusetts Institute of Technology, May 1995, Boston.
Magnet, Who's winning the information revolution, Fortune, Nov. 30, 1992, vol. 12, Issue 126, pp. 110-117.
Mallya et al., Correlation in rheumatoid arthritis of concentrations of plasma C3d, serum rheumatoid factor, immune complexes and C-reactive protein with each other and with clinical features of disease activity., Clin. Exp. Immunol., 1982, Issue 48, pp. 747-753.
Markoff, Making the PC come alive, New York Times, Sep. 1995.
Miller, Dial 1-900 for doctor, Newsweek, Oct. 1991.
Okada, Medical data base system with an ability of automated diagnosis, Computer Programs in Biomedicine, Sep. 1977, vol. 3, Issue 7, pp. 163-170.
Olson et al., $21^{st}$ century learning and health care in the home: creating a national telecommunications network, IAF/CRI, Jan. 1992.
Pauker et al., Towards the simulation of clinical cognition: taking a present illness by computer, Am. J. Med., Jun. 1976, vol. 7, Issue 60, pp. 981-996.
Riordan, Patents; Prodigy's patent is being debated as a possible threat to Sun Microsystems' Java language, New York Times, Feb. 1996.
Roberts, Dr. Schueler's home medical advisor 2.0, Compute!, Oct. 1992, Issue 145, pp. 106.
Shannon, Peripherals; choosing a college, New York Times, Jan. 1989.
Shannon, "Peripherals; advice on a disk: the doctor is really in", New York Times, Jul. 14, 1992 at C7.
Shannon, "Peripherals; Doctor, I have this funny pain . . . ", New York Times, Nov. 3, 1992.
Stearn et al., A statistical analysis of subjective and objective methods of evaluating fabric handle Part 2: Relationship between subjective and objective measurements, Journal of the Textile Machinery Society of Japan, 1988, vol. 2, Issue 34, pp. 39-46.
Szolovits et al., Categorical and probabilistic reasoning in medical diagnosis, Artificial Intelligence, Aug. 1978, vol. 1&2, Issue 11, pp. 115-144.

(56) References Cited

OTHER PUBLICATIONS

Tedesco, Microsoft, Intel and Sun advance NC visions, Broadcasting & Cable, Nov. 1996.
Templeton, Medical software that makes house calls, BusinessWeek, Jun. 1992, Issue 3720.
Vaughn et al., Effective algorithm-based triage and self-care protocols: quality medicine at lower costs, Ann. Emerg. Med., Jan. 1980, vol. 1, Issue 9, pp. 31-36.
Warner, Knowledge sectors for logical processing of patient data in the help system, Proc. IEEE, 1978.
Wijkstra et al., Relation of lung function, maximal inspiratory pressure, dyspnoea, and quality of life with exercise capacity in patients with chronic obstructive pulmonary disease, Thorax, May 1994, vol. 5, Issue 49, pp. 468-472.
Zallen, Member-centered managed care and the new media, ed. Linda M. Harris, in Health and the New Media, 1995.
Gardner, Integrated Computer Systems for Monitoring of the Critically Ill, Proceedings of 1st Annual Symposium on Computer Application in Medical Care, Washington, D.C., IEEE Computer Society, 1977, pp. 301-302.
Koska, Mary T., Primary Care: Hospitals Begin to Target Community Needs, Hospitals, Apr. 5, 1990, 64(7): 24-28.
The Alpha Media Catalog, Advertisement, Oct. 1993, "Physician's Database Manager" and "Iliad."
Arthur D. Little, Inc., Acorn Park, Cambridge, MA, Jul. 1992, "Can Telecommunications Help Solve America's Health Care Problems?" Summary.
Arthur D. Little, Inc., Acorn Park, Cambridge, MA, Jul. 1992, "Telecommunications: Can It Help Solve America's Health Care Problems?" pp. 1-116.
Becher, Ernst, "Fernmeldewesen für soziale Dienste in Entwicklungsländern," NTZ, 33:304, 1980.
Belzer et al., "Encyclopedia of Computer Science and Technology", Marcel Dekker, Inc., NY (US), 1978, pp. 78-79 and 114-115.
Bergman, "Computers make 'house calls' to patients; Harvard Community Health Plan offers computerized information service to patients," J American Hospital Association, 67(10): 52, May 20, 1993.
Bowden, K.F. et al., Information Processing, 71:1398-1406, 1972, "Data structures for general practice records."
Cimino, James J. et al., IEEE/Ninth Annual Conference of the Engineering in Medicine and Biology Society, 1987, "DXplain: An interactive knowledge base for assistance in medical diagnostic decisions."
Conrath, David W. et al., IEEE Transactions on Communications, COM-23(10):1119-1126, 1975, "A preliminary evaluation of alternative telecommunication systems for the delivery of primary health care to remote areas."
Currid, Cheryl, PC Week, Sep. 17, 1990, "Risky Business: doctors, lawyers shy away from computer technology."
Dahmer J., "Anamnese und Befund", Georg Thieme Verlag, 1981, pp. 22-25, 44-47, 292-295 and 371-375 (with English language translation of pp. 22-24, 44-45, 292, 295).
Dahmer J., Der Denkprozess "Vom Symptom zur Diagnose", Anamnese und Befund, Georg Thieme Verlag, 1981, p. 3 (with English language translation) pp. 3.
Doheny, Kathleen, La Times Magazine, p. 8, Aug. 4, 1991, "Hack attack."
Fisher et al., "Great Expectations: Expectation-based reasoning in Medical Diagnosis," Proceedings of the 12th Annual Symposium on Computer Applications in Medical Care, Nov. 6, 1988, pp. 38-42.
Frenger, Paul, IEEE Frontiers of Computers in Medicine, 1982, "Details of a database management system for a telephone medical consultation service."
Frenger, Paul, ISA, pp. 103-107, 1983, "Advanced techniques used to create a telephone medical consultation service."
Freudenheim, Milt, The New York Times, Business and Health, p. D2, Jun. 25, 1991, "Computer says take 2 aspirin."
Goldbard, Gary A, Class Notes, Tulane Medicine, Tulane University Medical Center, 1430 Tulane Avenue, New Orleans, LA 70112-2699, p. 26, Jun. 1991.
Gome, Amanda, Herald-Sun, p. 13, Nov. 19, 1991, "A picture of success."
Gorry, G. Anthony, Bulletin of the Operations Research Society of America, 19(2), 1971, "FA6.3 Automating Judgmental decision making in medicine."
"Harvard Community Health Plan Testing Computerized Service that Answers Health-Care Questions," Technical Computing, 6(9), Aug. 1991.
Hile, et al. "Reliability of an Automated Decision Support System for Behavioral Treatment Planning: Preliminary Results from the Mental Retardation-Expert", Computers in Human Services, 10(4): 19-29, 1994.
Hudson et al., "Human-Computer Interaction in a Medical Decision Support System." IEEE Computer Society Press, 2: 429-435, 1989.
Kerr, Jennifer, San Diego Union-Tribune, p. A3, Sunday, Jul. 18, 1993, "Phone is link to health-care information."
Larsson et al., "An Expert System Interface for an Identification Program," Automatica, Pergamon Press Ltd., Oxford, GB., 27(6): 919-930, 1991.
Laughlin, Michael L., ed., Computers in Health Care, pp. 32-37, Nov. 1992, "Telecommunications may offer poor a 'road' to healthcare."
Levin, Carol, PC Magazine, p. 32, Mar. 16, 1993, "Patient, heal thyself".
Mallory, Jim, Newsbytes, American Association for the Advancement of Science, Panel Discussion, Feb. 19, 1992, "Computers now giving medical advice."
McDonald et al., Environmental Science and Policy Institute, 1992, "Health in the Information Age: The Emergence of Health Oriented Telecommunication Applications."
"Netscape & Sun Announce Javascript The Open, Cross-Platform Object Scripting Language for Enterprise Networks and the Internet", Press Release, Dec. 4, 1995, web at http://java.sun.com/pr/1995/12/pr951204-03.html. (10 pages).
New York Times, p. 18, Jul. 13, 1991, "System helps doctors keep up to date."
O'Neil, et al., Conference Paper, IEEE Coll. on Computer Based Diagnosis, p. 8/1-4, 1989, "Diagnostic Support in the Oxford System of Medicine."
Rose, J, ed., "Progress of Cybernetics, vol. 2, Cybernetics and Industry, Social and Economic Consequences, Cybernetics and Artifacts," Proceedings of the First International Congress of Cybernetics, London, Gordon and Breach Science Publishers, pp. 803-811, 1969.
Rymon, et al., IEEE Transactions on Systems, Man, and Cybernetics, 23(6):1551-1560, Nov./Dec. 1993, "Progressive Horizon Planning-Planning Exploratory-Corrective Behavior."
Sacks, Terry, San Diego Union-Tribune, p. E-16, Mar. 24, 1992, "Pocket computer may cure technology-shy physicians."
Salvans, P. Ferrer and Alonso L. Vallès, Computer Biol. Med., 20(6):433-443, 1990, "An epidemiologic approach to computerized medical diagnosis—AEDMI program."
San Diego Emergency Physicians Society, Meeting Minutes, Regular Oct. 1991 Meeting, P.O. Box 16685, San Diego, CA 92176, first page.
Schild, W. et al., IBM J. Res. Develop., 22(5):518-532, 1978, "Computer-aided diagnosis with an application to endocrinology."
Shapiro, Encyclopedia of Artificial Intelligence, 2nd Edition, vol. 2, pp. 916-926, John Wiley & Sons, Inc., 1992.
Shortliffe, Edward H., Expert Systems and AI Applications, pp. 323-333, 1980, "Consultation system for physicians: the role of artificial intelligence techniques."
Sloane, L., New York Times, p. 16, Jul. 13, 1991, "For round-the-clock diagnosis, just pick up your telephone."
Smothers, R., New York Times, Sep. 16, 1992, "New video technology lets doctors examine patients many miles away."
Starr et al., "Gycon: A Microcomputer Based Gynecological Consultant," Proceed Inter Comp Symposium, Dec. 17-19, 1986, Tainan, Taiwan R.O.C. pp. 1678-1684.

(56) References Cited

OTHER PUBLICATIONS

Starr et al., "A microcomputer-based medical expert system shell using a weight/threshold decision mechanism," Proc. of the 13th Annual Northeast Bioengineering Conference, Mar. 12-13, 1987, pp. 279-281.
Szolovits et al., "Artificial Intelligence in Medical Diagnosis," Ann Intern Med., Jan. 1988, 108(1): 80-87; (pp. 1-12).
Thorpe, C. William et al., "A microcomputer-based interactive cough sound analysis system", Computer Methods and Programs in Biomedicine, Section II, Systems and programs, 36:33-43, 1991.
Wagner, J et al., Conference Paper of Expert Systems and Decision Support in Medicine, 33rd Annual Meeting of the GMDS EFMI Special Topic Meeting, pp. 449-465, Sep. 1988, "A knowledge-based system for interactive medical diagnosis encoding."
Walz, Nancy, The Associated Press, Business News, Jun. 25, 1991, "Computer system aims to wipe out medical paperwork."
Waterman, A Guide to Expert Systems, Addison-Wesley Publishing Co., pp. 46-47 and 272-288, 1986.
Weinstock, Edward, Cover, Avant-Garde, 1984, "An Apple a Day™."
Werner, et al., Conference Paper, IEEE Engineering in Medicine and Biology, 3 pages, 1989, "Interlocutor: Conferring with an Expert Diagnostic Consultant in Geriatric Psychiatry ."
EPO Examination Report dated Apr. 11, 2005 in European Patent Application No. 02075042.8, filed Jan. 7, 2002.
International Search Report and Written Opinion dated Feb. 21, 2007 in PCT/US06/24090, filed Jun. 20, 2006.
International Preliminary Report on Patentability dated Jul. 14, 2008 in PCT/US06/24090, filed Jun. 20, 2006.
Curtin et al. "Disease Management Information System: Design, Development, Testing, and Clinical Application for Cancer Management", Abstract http://ascobeta.infostreet.com/prof/me/html/abstracts/hre/m__1509.htm (1997).
Medical Computer Consultants' Consortium, Inc. "Disease State Management Software System *DMS2*—Product Description", http://www.mc3co.com/DMSS.htm (1997).
Memorial Sloan-Kettering Cancer Center "Center Develops New System for Disease Management" http://www.mskcc.org/document/cn950601.htm (1997).
Ball et al. Eds. Computers in Health Care: Aspects of the Computer-based Patient Record, Springer Verlag, 1992, pp. 1-336.
Barr et al., (Eds.) The Handbook of Artificial Intelligence, HeurisTech Press, 1982, vol. II, Chapter VIII, pp. 175-222.
Bischoff, A Knowledge Based System for Assisting in Differential Diagnosis of Chemically Dependent/Mentally Ill Patients, Computers in Human Services, 1992, vol. 8, Nos. 3/4, pp. 143-151.
Bortolan et al., The role of patient history in a decision support system, IEEE, Computers in Cardiology, Sep. 1990, Proceedings, pp. 357-360.
Brown et al., Information Infrastructure Task Force, The National Information Infrastructure: Agenda for Action, Sep. 15, 1993, pp. 26.
Christine, The Future of Health Care Technologies, HighBeam Research, Risk Management, Nov. 1, 1992, 1-3.
Common Carrier Week 8, Home Education and Health Benefits said to be underestimated, Warren Publishing Inc., Jan. 20, 1992, 9(3): 1-3.
Creative Strategies International (CSI), The Emerging Self-Help Healthcare Market—Microcomputer Applications, 1984, pp. 130.
Evans, C. Edward, A Computer in the Waiting Room: Who Needs the Doctor?, Can Fam Phys., Apr. 1984, 30: 869-876.
Fallon et al., A Primer for Writing Medical Data Base for the Clinical Decision Support System, Computers and Brains, Progress in Brain Research, Eds. Schadé et al., vol. 33, pp. 155-175.
Federal Register, National Telecommunications and Information Administration, DOC—Administration Policy Statement, Notices, Sep. 21, 1993, Fed. Reg., 58(181): 49025-49036.
First Opinion Corporation, Canadian Trademark Application File History TMA447,669, registered Sep. 15, 1995 for the Trademark/Servicemark: First Opinion, pp. 51.
Haug et al., Decision Support in Medicine: Examples from the HELP System, Computers and Biomedical Research, 1994, 27: 396-418.
Henderson, A Trainable Pattern Classifier for Medical Questionnaires, Annals of Biomed Engin., Jan. 27, 1972, 1: 115-133.
Johnson et al., Psychological Systems Questionnaire: An Objective Personality Test designed for on-line computer Presentation, Scoring, and Interpretation, Behav Res Meth Instrument., 1979, 11(2): 257-260.
Lunin, Lois F., On Speaking Terms With the Computer, Information Today, Feb. 1992, 9(2): 19-20.
Malcolm et al., Computer-Assisted Diagnosis of Alcoholism, Computers in Human Services, 1989, 5(3/4): 163-170.
McNish, David A., EMED Electronic Medical Database, DMC Software Packaging and Manual, DMC Software Company., 1987, 7 pages.
Miller et al., The Computerized Carroll Rating Scale, Indiana University School of Medicine, 1985, pp. 344-347.
Partin, A Preliminary Conceptual Framework for the Design, Development, and Use of Client-Oriented Information Systems in Health, J Med Sys. 1987, 11(2/3): 205-217.
Patel et al., A Computer-Based, Automated, Telephonic System to Monitor Patient Progress in the Home Setting, J Med Sys., 1992, 16(2/3): 101-112.
Shneiderman, Ben, Touch Screens now offer Compelling Uses, IEEE Software, 1991, pp. 93-94.
Shortliffe et al., A Model of Inexact Reasoning in Medicine, 1975, (shortened/editied version) Mathematical Biosciences, 11: 233-262.
Stead et al., Computer-Assisted Interview of Patients with Functional Headache, Arch Intern Med., 1972, 129: 950-955.
Szolovits et al., Guardian Angel: Patient-Centered Health Information Systems, May 1994, MIT Laboratory for Computer Science, TR-604, pp. 40.
The National Information Infrastructure: Agenda for Action, U.S. Government Paper, 1993, pp. 42.
Walmsley et al., Normal "Anion Gap" (Hyperchloremic) Acidosis, Case Reports, Clin Chem., 1985, 31(2): 309-313.
Weinstock, Edward, an Apple a Day . . . ™, Computer Program Manual, Avant-Garde Publishing Corporation, 1984, pp. 47.
Weiss et al., Glaucoma Consultation by Computer, Comput Biol Med . . . , Pergamon Press, 1978, 8: 2540.
Request for Ex Parte Reexamination filed Oct. 8, 2009 of USP 6,113,540, issued Sep. 5, 2000.

\* cited by examiner

| Cause/Anatomy Matrix | C1 | C2 | R | N | D1 | D2 | U1 | U2 | H | O | L | B | S | K | W | F |
|---|---|---|---|---|---|---|---|---|---|---|---|---|---|---|---|---|
| T | | | | | | | | | | | | | | | | |
| I | | | | | | | | | | | | | | | | |
| A | | | | | | | | | | | | | | | | |
| P | | | | | | | | | | | | | | | | |
| E | | | | | | | | | | | | | | | | |
| V | | | | | | | | | | | | | | | | |
| M | | | | | | | | | | | | | | | | |
| X | | | | | | | | | | | | | | | | |
| Y | | | | | | | | | | | | | | | | |
| N | | | | | | | | | | | | | | | | |
| Q | | | | | | | | | | | | | | | | |

200 → (header)
202 → (row)

Chief Complaints

- ☒ Abdominal Pain
- ☐ Altered mental status
- ☐ Back pain
- ☐ back pain, acute
- ☐ Chest pain
- ☐ Constipation
- ☐ Diaphoresis
- ☐ Diarrhea
- ☐ Diarrhea(not bloody)
- ☐ Dysphagia
- ☐ Dyspnea
- ☐ Fever
- ☐ Gastrointestinal bleeding
- ☐ Headache
- ☐ Jaundice
- ☐ Nausea/vomiting
- ☐ Pelvic pain
- ☐ Pelvic pain, acute
- ☐ Seizure
- ☐ Seizure > 20 minutes
- ☐ Seizure induction
- ☐ Seizures
- ☐ Seizures, refractory
- ☐ Splenomegaly
- ☐ Syncope
- ☐ Vaginal.
- ☐ Vertigo
- ☐ Weakness

FIG. 5

Cause/Anatomy Matrix

|   | C1 | C2 | R | N | D1 | D2 | U1 | U2 | H | O | L | B | S | K | W | F |
|---|---|---|---|---|---|---|---|---|---|---|---|---|---|---|---|---|
| T |   | X |   |   |   |   |   |   |   |   |   |   |   |   |   |   |
| I |   |   |   |   |   |   |   |   |   |   |   |   |   |   |   |   |
| A |   |   |   |   |   |   |   |   |   |   |   |   |   |   |   |   |
| P |   |   |   |   |   |   |   |   |   |   |   |   |   |   |   |   |
| E |   |   |   |   |   |   |   |   |   |   |   |   |   |   |   |   |
| V |   |   |   |   |   |   |   |   |   |   |   |   |   |   |   |   |
| M |   |   |   |   |   |   |   |   |   |   |   |   |   |   |   |   |
| X |   |   |   |   |   |   |   |   |   |   |   |   |   |   |   |   |
| Y |   |   |   |   |   |   |   |   |   |   |   |   |   |   |   |   |
| Z |   |   |   |   |   |   |   |   |   |   |   |   |   |   |   |   |
| Q |   |   |   |   |   |   |   |   |   |   |   |   |   |   |   |   |

FIG. 6

Top PHI = Open phi stems from all diseases

Display Phi Stems

Submit — show [All] [25] phi stems — from [All] [10] diseases — ☐ Show Top Disease — ☐ Auto SUBMIT

700

| Phi Stem | Y | N | U |
|---|---|---|---|
| Urinary frequency | Y | N | U |
| Psoas muscle spasm | Y | N | U |
| Hematuria | Y | N | U |
| Back pain | Y | N | U |
| Abdominal tenderness | Y | N | U |
| Abdominal swelling/distension | Y | N | U |
| Malaise | Y | N | U |
| Fatigue | Y | N | U |
| Gastrointestinal bleeding | Y | N | U |
| Weight loss | Y | N | U |
| Nausea/vomiting | Y | N | U |
| Syncope | Y | N | U |
| Weakness | Y | N | U |
| Tachycardia | Y | N | U |
| Shoulder pain, left side | Y | N | U |
| History of abdominal trauma | Y | N | U |
| Hypotension | Y | N | U |
| Constipation | Y | N | U |
| 30s | Y | N | U |
| 20s | Y | N | U |
| history of chronic constipation | Y | N | U |
| Age group 2_to 30s | Y | N | U |
| AGE > 50 | Y | N | U |
| Diarrhea | Y | N | U |
| Diaphoresis | Y | N | U |

List of Phis

Ulcerative colitis

Case phis are highlighted click Y | N | U to change

SUBMIT | Show Disease Elements

| Phi | Att = VALUE | Wt | Y | N | U |
|---|---|---|---|---|
| Gastrointestinal bleeding | 26 | y | n | u |
| Pyoderma gangrenosum | 26 | y | n | u |
| Weight Loss | 26 | y | n | u |
| Uveitis | 26 | y | n | u |
| Stress | 26 | y | n | u |
| Stools with Pus | 26 | y | n | u |
| Stools with Mucus | 26 | y | n | u |
| skin lesions | type = ERYTHEMA NODOSUM | 26 | y | n | u |
| Frequent bowel movements | 26 | y | n | u |
| Gastrointestinal bleeding | Type = LOWE | 26 | y | n | u |
| Cathartic use | 26 | y | n | u |
| Pregnancy | 26 | y | n | u |
| Erythema nodosum | 26 | y | n | u |
| Abdominal pain | onset = ACUTE | 26 | y | n | u |
| Episodic abdominal symptoms | 26 | y | n | u |
| Illness | 26 | y | n | u |
| Episcleritis | 26 | y | n | u |
| Diarrhea | severity = MILD | 26 | y | n | u |
| Diarrhea | quality = BLOODY | 26 | y | n | u |
| Hemorrhage | 26 | y | n | u |
| Conjunctivitis | 26 | y | n | u |
| Bloody stools | 26 | y | n | u |

FIG. 10

MATRIX INTERFACE FOR MEDICAL DIAGNOSTIC AND TREATMENT ADVICE SYSTEM AND METHOD

CROSS-REFERENCE TO RELATED APPLICATIONS

The benefit under 35 U.S.C. §119(e) of U.S. Provisional Application No. 60/621,384, filed Oct. 22, 2004, entitled "MATRIX-MDATA SYSTEM AND METHOD" is hereby claimed, and this application is incorporated by reference.

BACKGROUND OF THE INVENTION

1. Field of the Invention

The field of the invention relates to computerized medical diagnostic systems. More particularly, embodiments of the present invention relate to a computerized system and method for diagnosing a patient's medical complaint by utilizing the affected anatomic system and probable cause of the patient's medical complaint.

2. Description of the Related Art

Emergency physicians often have very little time and often even less information about a patient who is brought to the emergency department. Many errors occur because the physician may not consider all of the possible causes of the patient's complaints. A list of the possible diagnoses that a patient can have is called a differential diagnosis.

A few examples will help define the problem. For instance, a patient may be brought in comatose with a high fever. The emergency physician needs to know immediately, sometimes within seconds the causes of coma and particularly the causes of coma that could be caused by infection.

For example, a patient may exhibit a cough and a fever. A logical assumption would be that the patient has an infection (cause) in the respiratory system (anatomic system).

For example, a patient may be brought to the ER in a coma and there may be no history other than that he works in a garage indicating possible carbon monoxide poisoning.

Further, the best testing strategy to distinguish between several possible diagnoses has to be planned in, again, very little time.

What is desired is a way to allow a clinician to start an evaluation based on the limited information that is available. This frequently occurs in emergency medicine, where there are significant constraints on time and information.

There are other occasions when medical personnel have more time to obtain detailed information from and about the patient, and/or the patient can provide additional information by themselves. In these circumstances, a detailed fully automated approach to developing a diagnosis is desired. There are yet other occasions when various combinations of the above are desired depending on the time and information available.

SUMMARY OF CERTAIN INVENTIVE ASPECTS

In one embodiment of the invention, there is an automated medical diagnostic system, comprising a graphical user interface (GUI) comprising a matrix of cells, each cell being representative of a patient health item (PHI) associated with a particular disease; a plurality of diagnostic functions that uses the matrix for input and output, wherein the diagnostic functions are selectively executed according to each newly input PHI so as to result in and display a differential diagnosis.

A disease may be an abnormality, affliction, ailment, anomaly, disorder, illness, indisposition, infirmity, malady, problem or sickness of a patent. The system may use a Meta analysis of the input PHIs.

The system may use a reenter function so as to request a user of the system to consult the system at a later time.

A PHI may be a sign, symptom, complaint, presentation, manifestation, finding, laboratory test result, home test result, or an interpretation of an imaging study.

The GUI may be configured for use by a trained health professional.

The system may be configured for use by physicians, physician's assistants, nurses, paramedics, emergency medical technicians, veterinarians, chiropractors, dentists, optometrists, and holistic health providers.

The system may use software objects.

Scoring and thresholding may be used by at least one of the diagnostic functions.

The differential diagnosis may be a single disease.

The diagnostic functions may form a list-based processing system.

The diagnostic functions may use a patient medical record.

The system may run on a handheld computing device, a personal digital assistant (PDA) or similar computing device.

The onset time shape of a PHI may be captured in a graphical manner in which the x axis represents time and the y axis may represent severity.

The change in intensity of a PHI over time may be graphically displayed on the GUI.

The variability of any aspect of a PHI can be expressed graphically and this image transformed into information to diagnose a disease.

The interrelationships of PHIs over time may be input from a Gantt chart based input system.

The value of one PHI may be varied by a process of sensitivity analysis, producing changes in the differential diagnosis of a set of PHIs.

The total amount of time the patient has presented a PHI or condition may be input graphically and the area under a corresponding curve may be determined by integrating the graphed function.

When a patient indicates their condition begins to improve, the system may cause a specific action or may stop a particular consultation to allow more time to elapse to determine if a trend continues.

The topographic area of a patient's complaint(s) may be indicated on an avatar displayed by the GUI which then causes different diagnostic weights to be added to various diseases.

The sensitivity of a consultation can be varied by levels such that a number and area of specialty interest of diseases considered in a consultation can be increased in steps from urgent and common diseases to all diseases known to mankind. The matrix may be used to specify the levels and the area of specialty interest.

All human diseases stored in the system may be considered in the differential diagnosis.

A patient's incidental symptoms may be saved and evaluated at a later time in a different context.

An ongoing disease process may be distinguished from a disease process in which the symptoms have disappeared.

Each PHI may have associated questions to establish the PHI, and diagnosis may occur in two different modes, including a horizontal axis of inquiry (HAI) mode in which the questions for each PHI may be selected with the understanding that several diseases are under diagnostic consideration, and a vertical axis of inquiry (VAI) mode in which one disease may be the source of all the questions for each PHI or in which one disease may be the focus of inquiry. Diseases in the HAI may be segregated into a subset for further focused evaluation in which all questions may be taken from the subset of diseases. The system may start operation in HAI mode and then turn to VAI mode upon certain criteria being met, or it may start in VAI mode, usually with the most urgent diagnosis under consideration.

The diseases may be weighted if a PHI matches.

The attributes of a PHI may be evaluated to further define the PHI and in which diagnostic weight may be sequentially added depending upon the number of matching attributes.

Each PHI in the system may be represented by a portion of an inverted tree with a basic and general PHI at the root of the tree and a detailed and specific PHI or PHI attribute at the leaves of the tree. Diagnostic weight may be sequentially added as a more precise match is made as the questioning proceeds down the tree. PHIs may be hierarchically weighted based upon their position in the tree.

The relationships between risk factors, causes, and complications of a disease may be graphically displayed, with the x-axis being time, by the GUI.

The interrelated causality of diseases may be expressed graphically and dynamically.

Geographical information related to the PHIs may be entered on a graphic image of a world map.

A patient work up may be automatically planned to diagnose one disease from a set of possible diseases.

Questions may be presented directly to the patient. An interactive Gantt chart may be used to express the relationships between various PHIs in a disease with respect to time and that information may be used to diagnose the patient.

A disease may be defined or represented by a Gantt chart displayed by the GUI.

One or more predetermined PHIs may be displayed and immediately selected if they should occur during an interview process of a consultation which may cause a change in the execution path of the system or may cause another action to take place.

Potentially dangerous situations may be automatically recognized and a metric of the potential danger to the patient may be graphically displayed by the GUI.

Potentially dangerous situations may be automatically recognized and a metric of the potential danger to the care giver may be graphically displayed by the GUI.

A feedback loop may exist in which at least one diagnostic weight corresponding to at least one PHI may be automatically changed based on data obtained by usage of the system over time.

In another embodiment of the invention, there is an automated medical diagnostic method, comprising displaying a matrix of cells, each cell being representative of a patient health item (PHI) associated with a particular disease; entering a PHI on the display in one of the cells; updating a differential diagnosis based on the input PHI; and displaying the updated differential diagnosis.

The displaying may be performed via a graphical user interface (GUI). The GUI may be configured for use by a trained health professional.

A PHI may be a sign, symptom, complaint, presentation, manifestation, finding, laboratory test result, home test result, or an interpretation of an imaging study.

The method may be configured for use by veterinarians, chiropractors, dentists, optometrists, or holistic health providers.

The updated differential diagnosis may be a single disease.

The method may additionally comprise storing the input PHI in a patient medical record.

The method may be performed on a handheld computing device, a personal digital assistant (PDA) or a PDA-like computing device.

The method may additionally comprise presenting questions corresponding to at least one PHI directly to the patient.

In another embodiment of the matrix, the X-axis presents standard anatomic systems and the Y-axis shows the different parts of a workup. These being, chief complaints, history of the present illness, past medical history, family medical history, social history, vital signs, physical examination findings, lab tests, special studies, imaging, and treatment. By selecting a cell, for example, the cell at the intersection of respiratory system and chief complaints, all of the chief complaints related to the respiratory system would be displayed.

BRIEF DESCRIPTION OF THE DRAWINGS

FIG. 1 is an exemplary screen display of an embodiment of a graphical user interface (GUI) utilized in a matrix-medical diagnostic and treatment advice (MDATA) system.

FIG. 2 is an exemplary screen display of an embodiment of a two dimensional matrix used by the GUI.

FIG. 5 is an exemplary screen display of an embodiment of a chief complaints input panel used by the GUI.

FIG. 6 is an exemplary screen display of an embodiment of an anatomic system and cause matrix showing a selected cell as used by the GUI.

FIG. 7 is an exemplary screen display of an embodiment of a batch mode response to questions (for PHIs) input panel used by the GUI.

FIG. 9 is an exemplary screen display of an embodiment of a candidate selection options input panel used by the GUI.

FIG. 10 is an exemplary screen display of an embodiment of a disease object panel used by the GUI.

DETAILED DESCRIPTION OF CERTAIN INVENTIVE EMBODIMENTS

Figure 3:
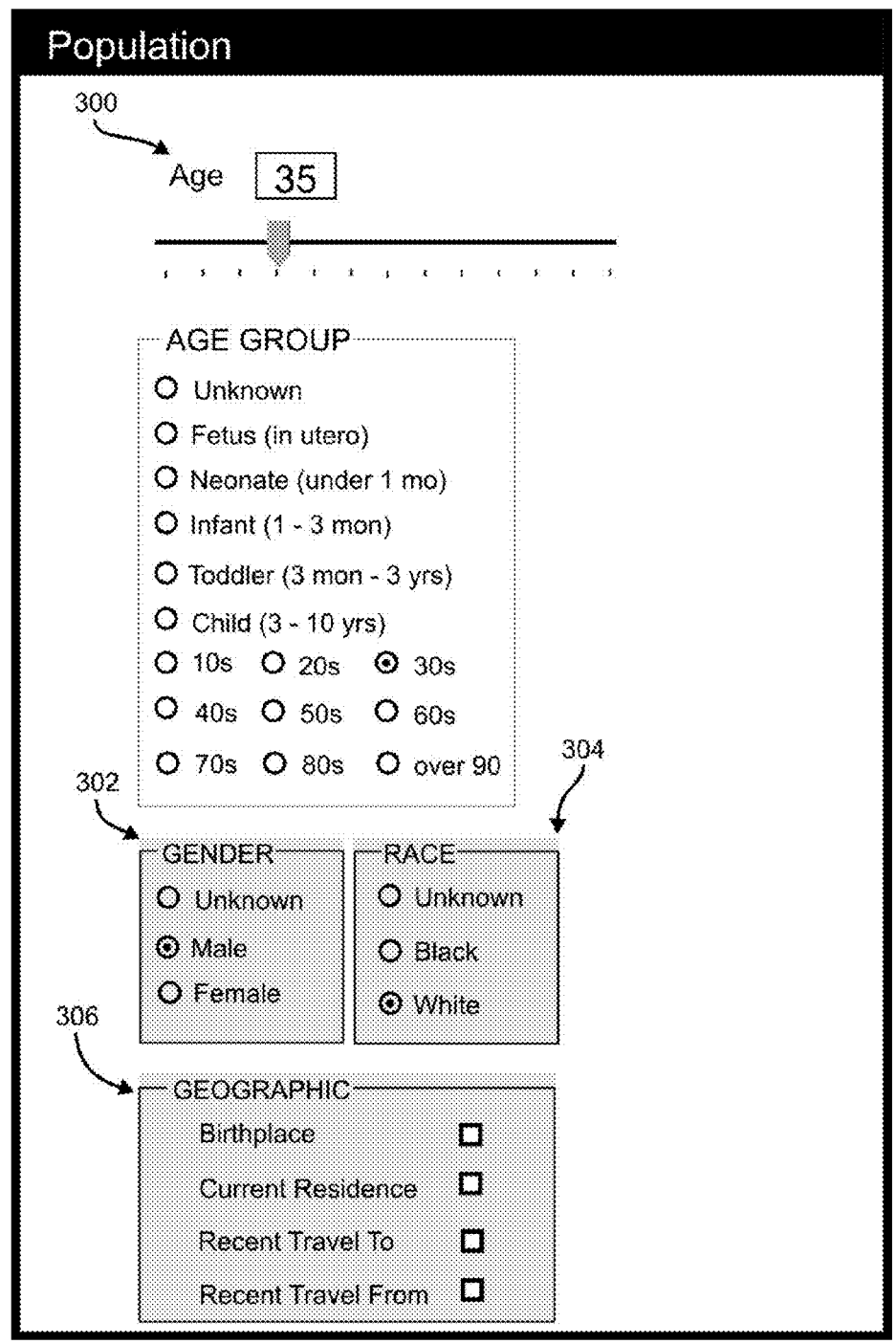
FIG. 3 is an exemplary screen display of an embodiment of a population input panel used by the GUI.

The following description presents certain specific embodiments of the present invention. However, the present invention may be embodied in a multitude of different ways as defined and covered by the claims. In this description, reference is made to the drawings wherein like parts are designated with like numerals throughout.

A matrix-medical diagnostic and treatment advice (MDATA) embodiment of the First Opinion fully automated patient specific diagnostic and treatment advice system will be described. The matrix-MDATA (MM) system runs on any computer but is designed to be used by a healthcare giver during a bedside interaction with a patient. An exemplary configuration of components is described hereinbelow.

The MM system is designed to provide the correct diagnosis at the earliest possible point in time while asking the fewest number of questions. The MM system combines the MDATA system, such as described in U.S. Pat. Nos. 5,660,176, 5,935,060, 6,022,315, and 6,527,713, with the Matrix system, such as described in U.S. patent application Ser. No. 10/862,116, and which are all hereby incorporated by reference.

The MM system may be used in a fully automated mode, reflecting the MDATA system, or in a health care giver mode, reflecting the Matrix system, or any combination of the two modes.

The MM system is comprised of various modules, tools, and applications as discussed in detail below. As can be appreciated by one of ordinary skill in the art, each of the modules may comprise various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system modules, tools, and applications may be written in any programming language such as, for example, C, C++, BASIC, Visual Basic, Pascal, Ada, Java, HTML, XML, or FORTRAN, and executed on an operating system, such as variants of Windows, Macintosh, UNIX, Linux, VxWorks, or other operating system. C, C++, BASIC, Visual Basic, Pascal, Ada, Java, HTML, XML and FORTRAN are industry standard programming languages for which many commercial compilers can be used to create executable code.

Definitions

The following provides a number of useful possible definitions of terms used in describing certain embodiments of the disclosed invention.

A network may refer to a network or combination of networks spanning any geographical area, such as a local area network (LAN), wide area network (WAN), regional network, national network, and/or global network. The Internet is an example of a current global computer network. Those terms may refer to hardwire networks, wireless networks, or a combination of hardwire and wireless networks. Hardwire networks may include, for example, fiber optic lines, cable lines, ISDN lines, copper lines, etc. Wireless networks may include, for example, cellular systems, personal communications service (PCS) systems, satellite communication systems, packet radio systems, and mobile broadband systems. A cellular system may use, for example, code division multiple access (CDMA), time division multiple access (TDMA), personal digital phone (PDC), Global System Mobile (GSM), or frequency division multiple access (FDMA), among others.

A website may refer to one or more interrelated web page files and other files and programs on one or more web servers. The files and programs are accessible over a computer network, such as the Internet, by sending a hypertext transfer protocol (HTTP or HTTPS [S-HTTP]) request specifying a uniform resource locator (URL) that identifies the location of one of said web page files, wherein the files and programs are owned, managed or authorized by a single business entity. Such files and programs can include, for example, hypertext markup language (HTML) files, common gateway interface (CGI) files, and Java applications. The web page files preferably include a home page file that corresponds to a home page of the website. The home page can serve as a gateway or access point to the remaining files and programs contained within the website. In one embodiment, all of the files and programs are located under, and accessible within, the same network domain as the home page file. Alternatively, the files and programs can be located and accessible through several different network domains.

A web page or electronic page may comprise that which is presented by a standard web browser in response to an HTTP request specifying the URL by which the web page file is identified. A web page can include, for example, text, images, sound, video, and animation.

A computer or computing device may be any processor controlled device that permits access to the Internet, including terminal devices, such as personal computers, workstations, servers, clients, mini-computers, main-frame computers, laptop computers, a network of individual computers, mobile computers, palm-top computers, hand-held computers, set top boxes for a television, other types of web-enabled televisions, interactive kiosks, personal digital assistants (PDAs), interactive or web-enabled wireless communications devices, mobile web browsers, or a combination thereof. The computers may further possess one or more input devices such as a keyboard, mouse, touch pad, joystick, pen-input-pad, and the like. The computers may also possess an output device, such as a visual display and an audio output. One or more of these computing devices may form a computing environment.

These computers may be uni-processor or multi-processor machines. Additionally, these computers may include an addressable storage medium or computer accessible medium, such as random access memory (RAM), an electronically erasable programmable read-only memory (EEPROM), programmable read-only memory (PROM), erasable programmable read-only memory (EPROM), hard disks, floppy disks, laser disk players, digital video devices, compact disks, video tapes, audio tapes, magnetic recording tracks, electronic networks, and other techniques to transmit or store electronic content such as, by way of example, programs and data. In one embodiment, the computers are equipped with a network communication device such as a network interface card, a modem, or other network connection device suitable for connecting to the communication network. Furthermore, the computers execute an appropriate operating system such as Linux, UNIX, any of the versions of Microsoft Windows, Apple MacOS, IBM OS/2 or other operating system. The appropriate operating system may include a communications protocol implementation that handles all incoming and outgoing message traffic passed over the network. In other embodiments, while the operating system may differ depending on the type of computer, the operating system will continue to provide the appropriate communications protocols to establish communication links with the network.

The computers may contain program logic, or other substrate configuration representing data and instructions, which cause the computer to operate in a specific and predefined manner, as described herein. In one embodiment, the program logic may be implemented as one or more object frameworks or modules. These modules may be configured to reside on the addressable storage medium and configured to execute on one or more processors. The modules include, but are not limited to, software or hardware components that perform certain tasks. Thus, a module may include, by way of example, components, such as, software components, object-oriented software components, class components and task components, processes, functions, attributes, procedures, subroutines, segments of program code, drivers, firmware, microcode, circuitry, data, databases, data structures, tables, arrays, and variables.

The various components of the system may communicate with each other and other components comprising the respective computers through mechanisms such as, by way of example, interprocess communication, remote procedure call, distributed object interfaces, and other various program interfaces. Furthermore, the functionality provided for in the components, modules, and databases may be combined into fewer components, modules, or databases or further separated into additional components, modules, or databases. Additionally, the components, modules, and databases may be implemented to execute on one or more computers.

Exemplary MM System Configuration

Figure 26:
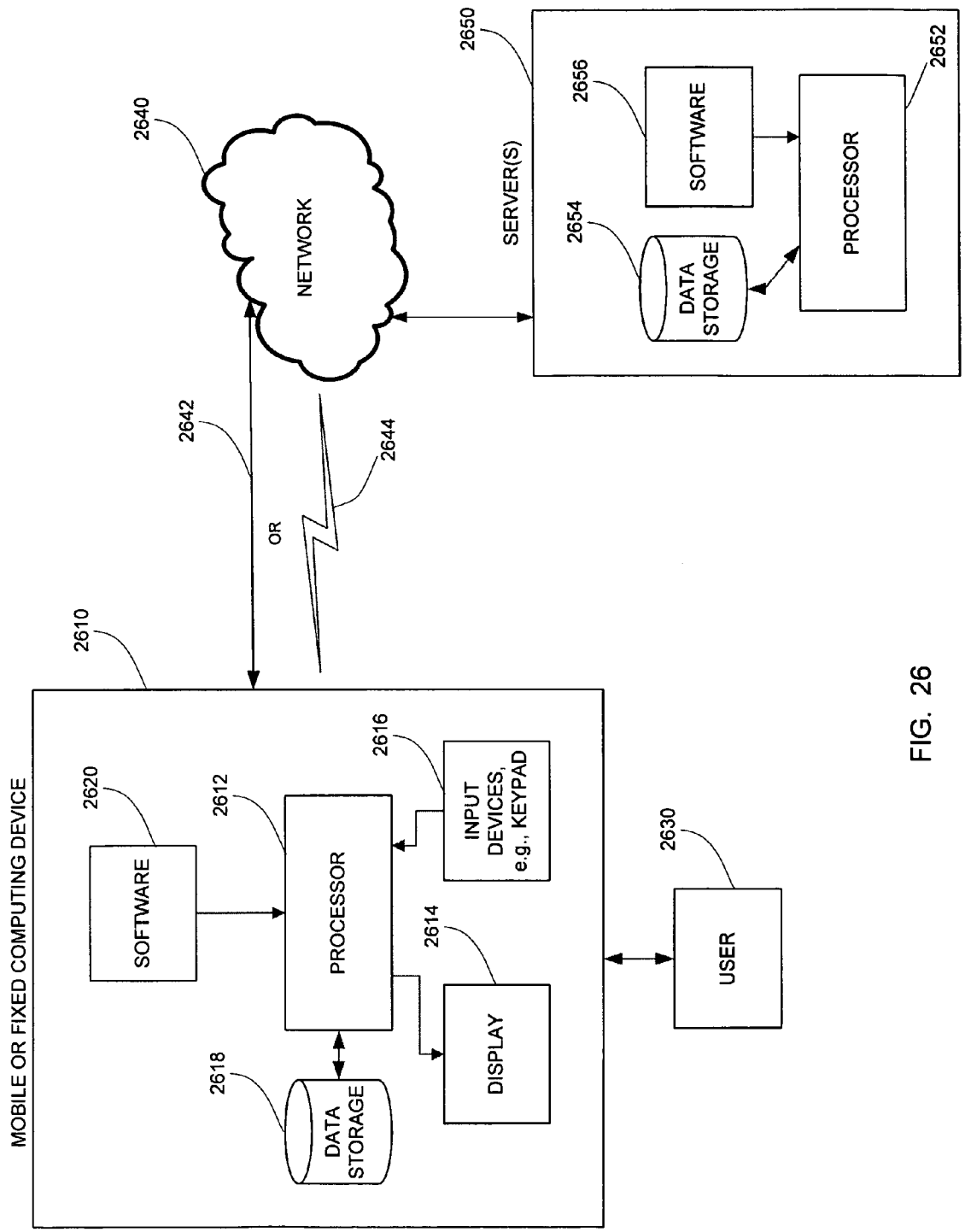
FIG. 26 is a block diagram of an exemplary configuration of components of an embodiment of the Matrix-MDATA system.

Referring to FIG. 26, an exemplary configuration 2600 of components of an embodiment of the MM system will now be described. A mobile or fixed computing device 2610 is operated by a user 2630. The computing device 2610 can be a handheld computing device or other portable computing device such as a Palm, Pocket personal computer (PC), Linux based handheld, PDA, Tablet PC, or PC having a display. The computing device 2610 in certain embodiments operates in a stand-alone (independent) manner. In other embodiments, the computing device 2610 is in communication with one or more servers 2650 via a network 2640. The server(s) include one or processors 2652, data storage 2654 and system software 2656 executed by the processor(s). In certain embodiments, the data storage 2654 stores one or more databases used by the system, and stores patient medical records. The processor(s) 2652 are in communication with the database(s) via a database interface, such as structured query language (SQL) or open database connectivity (ODBC). In certain embodiments, the data storage 2654 is not included in server(s) 2650, but is in data communication with the server(s) via the database interface. The connection from the computing device 2610 to the network 2640 can be a wireless or a satellite connection 2644 or a wired or direct connection 2642. In certain embodiments, the server(s) are part of a web site, such as on an intranet or the Internet.

When the computing device 2610 is connected with the server(s) 2650, the web site may optionally provide updates on new disease information or about new laboratory tests, special studies, imaging modality of choice and treatment of choice. In addition, the computing device 2610 can optionally be linked to the network 2640 to allow instantaneous reporting of and downloading information about, for example, possible epidemics or the use of weapons of mass destruction (WMD). In another embodiment, the computing device 2610 runs only when connected to the server(s) 2650.

The computing device 2610 includes a processor 2612, a display 2614, and one or more input devices 2616. The processor 2612 is in data communication with a data storage 2618 for storing one or more databases having medical data used by the system. In certain embodiments, the data storage 2618 stores patient medical records. System software 2620 is executed by the processor 2612. The system software 2620 includes an application graphical user interface (GUI). The application GUI can include a database interface to the data storage 2618 of the computing device. In certain embodiments, the software is loaded from the data storage 2618. In embodiments where the computing device 2610 communicates with a web site, the processor utilizes browser software in place of or in addition to the software 2620.

Overview of Object-Based Diagnosis

In computer software terms, an object is combination of data and processes that manipulate the data. The data are said to be "encapsulated," meaning that the data is hidden, so that a user of the object only sees processes that can be invoked. Using an object's processes, one can then manipulate the data without having to know the exact location and format of the data. When more than one copy of the object is required, one can make copies of the data, but use the same process set to manipulate each of the copies as needed. This set of processes can then be thought of as an "engine" that controls or represents the objects' behavior, whether there are 10 or 10,000 object copies.

This section describes a diagnostic paradigm that uses software objects to establish a broad, generalized software environment for medical diagnosis, which is used to define and develop the programming elements of medical diagnosis. The objects are then used to guide and control the diagnostic process, to conduct the patient interview, to perform related analytical tasks, and to generate the diagnoses. A software object is a fundamental software structure that can be used to organize the processes and data of a computer program in such a way as to make possible very complicated applications. This description will discuss novel uses of object oriented programming (OOP) in medical diagnosis, such as the use of software objects for the purpose of fully automated medical diagnosis, the entire/overall method of dynamically assembling the components of diagnosis in the form of objects, and then letting the objects interact to compute a diagnosis.

Defining and creating software objects is well-known to any programmer trained in object-oriented programming. Using an OOP-capable compiler, the programmer defines the data that represent the object and the actions that the object can perform. At run time, the program creates an object, supplies the data that define the object, and then manipulates the object using the object actions. The program can create any number of objects as needed. Each object can be independently initialized, manipulated, and destroyed.

In the object-based (OB) method discussed here, software objects are used as active, intelligent agents that represent all of the players and all of the data in suitably organized roles. It is important to note in this metaphor that all of the disease objects, which are "specialists" for a single disease, are allowed to monitor the questions and answers of other objects.

One key concept of the OB method is to think of disease and symptom objects as representing the medical experts inside the computer. If we ask the Appendicitis Disease Object to look at a patient, the object looks at the patient data, notes that the patient does indeed complain of abdominal pain and nausea—but then "notices" the appendectomy scar! This indicates that appendicitis can probably be ruled out, so VAI would step down and return control to HAI so that another more likely diagnosis can be considered first. In this case HAI might invoke another VAI expert, say, Small Bowel Obstruction. That object takes a look, asks some questions, and renders its opinion on the probability of it being the diagnosis. In effect, a huge number of diagnostic experts are gathered at the patient's bedside, and each object may get a turn at evaluating the patient data in terms of its own symptom pattern.

As an actual patient symptom set is built up, disease objects judge themselves and return a probability that they are the correct diagnosis. The emergent effect is a patient interview and a diagnostic evaluation that—by design—constantly stays focused on the most likely set of diseases of the patient. Carefully focused questions are used to eliminate or reduce the likelihood of diseases, to promote others into the "realm of suspicion," and to expand the search in a promising direction, based on the data being obtained from the patient.

In this example, the disease object can make time-based recommendations to the system or the patient. This "advice" can then be used as part of a report to the user or the patient as "discharge instructions".

A software "object" is basically a data structure plus associated processes that can do things with, for or to the data. An important property of an object is that the object's data can be hidden behind the object's processes, so that the outside user of the object can only see and use object processes that can be invoked to access the data. The object is said to "hide" data; it provides the powerful ability of decoupling the world that uses an object from the object itself.

A. Disease Object

A Disease Object (DO) is a software object that represents an abnormal health state (illness, disease, disorder, or cause) which is collectively called a "disease." It is used in the system and method to establish the likelihood that the specified disease exists in the current patient.

B. Symptom Object

A Symptom Object (SO) is a software object that represents a patient health item (sign, symptom, complaint, presentation, manifestation, finding, laboratory test result (home or remote), and interpretations of an imaging study) which is collectively called a symptom or a PHI (Patient Health Item). It is used in the system to describe patient health in terms that the list-based (LB) system can use for diagnosis. It is important to note that PHI may be a synergy. Synergies are combinations of other PHIs either occurring together or sequentially which make one disease more likely than another. A simultaneous synergy is the occurrence of two or more PHIs occurring at the same time. A sequential synergy occurs when two or more PHIs occur in a certain time sequence. A summation synergy is a combination of other synergies.

C. Valuator Object

A Valuator Object (VO) is a software object that represents the actions required to establish the value of a symptom in a patient at a specified time.

D. Question Object

A Question Object (QO) is a software object that describes the software elements required to establish a mini-dialog of questions and responses with the patient, in order to obtain a symptom value. It is the task of the QO to select the appropriate question set, to invoke the appropriate node objects that actually question the patient, and to report back the patient's response. A QO is a type of valuator object that specializes in interaction with a patient.

E. Node Object

A Node Object (NO) is a software object that describes the software elements required to ask a single, well-defined question of the patient and to return the response selected by the patient. It is the task of the NO to present the required data to the GUI in a form that will appear in a user-friendly manner on the user display, to wait an appropriate amount of time for a user response, to possibly re-prompt the user, and to ultimately return the user's response.

Brief Review of MDATA System

A fear of many patients is that they may have a disease that their doctor is not familiar with. The advantage of an automated system is that it is as easy to consider 2000 diseases as it is to consider 20 diseases. The MM system can be customized to consider only the most urgent, serious and common diseases, or to consider every disease of mankind. While not technically true, the point is clear. It is simply not possible for any human being to be familiar with every disease, let alone be able to diagnose it. But a fully automated system such as the MM system can consider every disease of mankind in every consultation.

The MDATA system includes a computer program that is designed to conduct a question and answer dialog with a human patient for the purpose of eliciting medical symptoms and then generating a list of possible illnesses suggested by the symptoms.

The MDATA system includes a comprehensive database of suitably formatted medical knowledge plus a driver program that conducts the interview, accesses the database, and interfaces with the user at run time.

The MDATA system is fully automated; no other human is involved at runtime other than the human user, who is assumed to be a patient or a patient representative such as a parent who is familiar with the patient/symptoms.

The MDATA system can, of course, also be used by medical students, nurses, even doctors who are willing to project themselves into the role of a patient. However, keeping in mind the purpose of the MDATA system, its medical terminology and style of questioning will tend to appear plodding, amateurish, and tedious to medical staff that, in recent decades, have lost the luxury of spending several hours at a time with a single patient.

The MDATA system output can be forwarded to a human MD, to another computer program for further use, and to the patient's medical record for continuing care such as follow-up or disease management.

Brief Review of Matrix System

A healthcare giver can quickly identify a disease using the Matrix system. This is done by entering chief complaints and other available information such as the cause and anatomic system.

The Matrix system provides a "population" specific differential diagnosis. Population specific refers to the age, sex, race, location, work place, travel history of the patient, etc. The Matrix system allows the user to look at disease information by an anatomic system that the disease may occur in, the possible causes of a problem, the chief complaint, by age groups, by gender, etc. The Matrix system allows the user to dynamically change the sorting parameters themselves. The Matrix system is fast, easy to use and structures the information in such a way as to be meaningful to a clinician at the bedside. The Matrix system can adjust to the sophistication of the user. For example, there are versions for Emergency Medical Technicians (EMTs), Nurses, Primary care physicians, Emergency Physicians, and Specialists.

Section I: Brief Review of Clinical Decision Making

There are four different levels of clinical decision making used in the diagnostic process. Each of these levels is represented or modeled by one or more of the MM system features.

The most basic level is pattern matching, sometimes called a "nearest neighbor" analysis. In this method, the PHIs (Patient Health Items) of a patient are simply matched to the PHIs of different diseases, and the one that most matches is the most likely diagnosis.

In certain embodiments, this is exactly where the MM system begins its diagnostic process. The initial differential diagnosis is assembled from the key words selected by the patient and the chief complaint set selected by the user. Each PHI is weighted differently in each disease, and, in the fully time-based system, weighted differently for each part of the disease time line.

The second level of clinical decision making is the "rule-based" method. In certain embodiments, rules refer to "if/then" statements, algorithms, or check lists. The algorithmic aspect of the MM system models this. So do the rules that are used by the diagnostic engine or list-based engine in dynamically sequencing questions. This process takes the following diagnostic aspects of the diseases into consideration: relativity, urgency, seriousness, and prevalence.

The third level of clinical decision is the "Hypothetical-Deductive Process". The process of hypothesis generation, evaluation and refinement is modeled in the different axis of inquiry modes and a disease segregation feature.

The Axis of Inquiry (AOI) concept is where, in Horizontal Axis of Inquiry (HAI) mode, each disease object "votes" for what question it wants to ask to help clarify the disease. The list-based engine sequences the questions based upon several different diagnostic strategies. Each PHI is weighted differently in each disease, and as each question is asked and answered, the diagnostic weight of the PHIs, either positive or negative, is added. This continues until a threshold is reached, and one of the disease objects seems to be the most likely candidate. The threshold is related to the diagnostic score but also to how rapidly it is rising. At this point (threshold), the system goes into the Vertical Axis of Inquiry (VAI) mode.

In VAI, one disease object controls the sequence of the questions asked. The hypothesis is that the disease that is currently being evaluated is the diagnosis. If this assumption proves wrong, the system returns to the Horizontal Axis of Inquiry (HAI), in which other diseases are again considered in the differential diagnosis.

The fourth kind of clinical decision making is called the naturalistic or event-driven process. Here, certain situations (rather than diagnoses) are used to alter the diagnostic process. This frequently involves treating a patient's symptoms and signs before any diagnosis is known. This process can be seen in the Action Plateau, Nexus Point, Symptom Watch, and Treatment Finesse features, described below.

When a set of clinical PHIs suggest a situation that could require immediate attention, the Action Plateau (AP) function recognizes the situation and notifies the caregiver or patient.

There are some Meta heuristics built into the architecture of the MM system. For example, the system always considers the most urgent conditions first, even if their probability might delay their consideration. In one embodiment, the Treatment Finesse feature of the MM system always maximizes the therapeutic window of opportunity. In addition, the system weights all of the diseases in the differential diagnosis each time a PHI is established. That is referred to in the system as parallel processing or list-based processing.

A. Diagnostic Engine—Disease Segregation and Special PHI Designations

Several improvements have been made to the diagnostic system. A significant improvement is that the diagnostic system is now able to segregate diseases into several categories. This helps to speed the diagnostic process by reducing the number of questions that are asked of the patient without losing sensitivity. There are several ways disease segregation is implemented.

Firstly, when a disease can no longer reach diagnostic threshold, it is designated impossible to rule in at this time. Therefore, this disease is no longer considered in the differential diagnosis and is no longer allowed to suggest PHIs to the system.

Secondly, a typical diagnostic process would consider between 3 and 6 candidate diseases. Each of these diseases has a diagnostic score, and the rate of rise of diagnostic scores and number of hits make them most likely to be the diagnosis.

Thirdly, when a threshold is reached, the diseases that do not reach or exceed this threshold are "segregated" out of the diagnostic process. These segregated diseases are no longer able to "suggest" questions to be asked. Each time a PHI is established, however, if it occurs in the segregated diseases, it will be appropriately weighted. Further, diseases continuously being segregated out and then integrated back into the diagnostic process are most likely candidate diseases.

Certain PHIs now have special designations in a disease. They are as follows:
  Late stage symptom
  Critical curve symptom
  First expected symptom
  Diagnostic point symptom Besides the diagnostic weight, each PHI is given a "sine qua non" or "sine" score in each disease. This has to do with how important it is for the PHI to be present in order to have enough evidence to make a clinical diagnosis. The following are examples of the sine designations:
  Pathognomonic
  Sine qua non—major
  Sine qua non—minor
  Wanted strongly
  Wanted
  Helpful If a pathognomonic PHI is present, the disease is diagnosed. For example, seeing fortification figures before a headache is pathognomonic for migraine headache. That means that if the patient has this PHI then the patient has this disease because that PHI is 100% specific. Sine qua non—major means that that PHI or a specific number of PHIs out of a limited set of PHIs must be present for the diagnosis to be made.

The MDATA diagnostic engine can be referred to as the diagnostic engine or the list-based processor. The function of the engine is finding the next best question(s) to present to the user to be evaluated.

As discussed, diseases that cannot be ruled in are segregated out of the interaction and diseases that are lagging behind the main candidate disease are no longer allowed to suggest PHIs.

Once the VAI threshold is reached, the effective candidate disease set has been narrowed down to one. This is because in VAI, only one disease object proposes questions to be evaluated. However, all diseases in diagnostic consideration are still being weighted.

B. Features of the MM System

Figure 1:
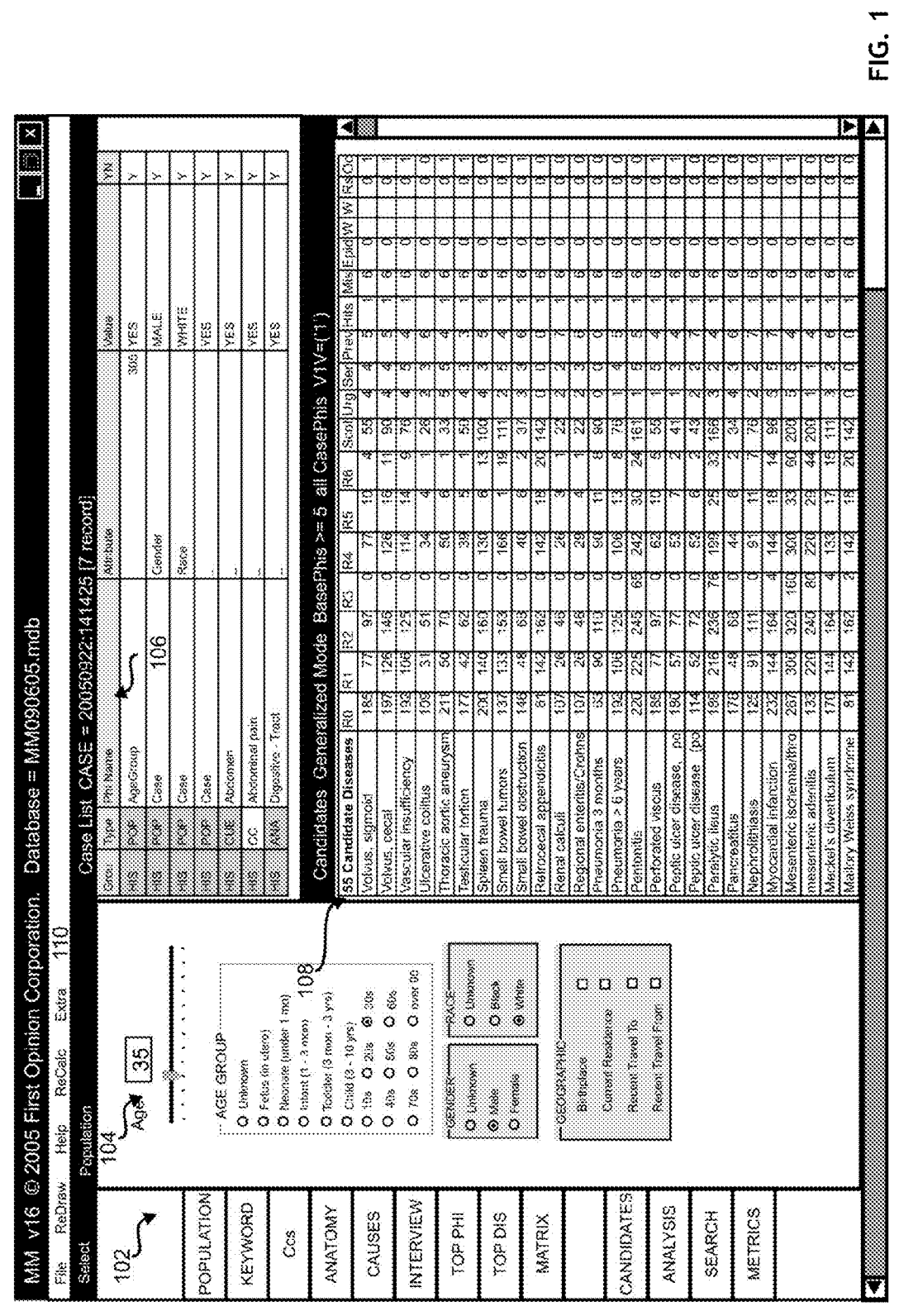

The MM system's main screens are originally composed into five parts:
- Data entry including Matrix tabs
- Case
- Differential with focused subset differential
- Disease object
- Interview pane Referring to an exemplary main screen display shown in FIG. 1, there are several different default positions of the windows or panes, which can be customized. In certain embodiments, all data input can be accomplished by tapping the screen with a pen input device, clicking a mouse, or typing on a keyboard. Interactive Voice Response (IVR) and Automatic Speech Recognition (ASR) are currently not used as input media as in earlier MDATA embodiments, but may be available in future embodiments. A data entry pane 104 consists of a series of tabs. Each tab can be selected by clicking on the appropriate button on a toolbox 102.

A case pane 106 contains the relevant clinical information about the patient. This comes either from the patient's medical record (if available) or the information acquired from the interaction with the patient or health care worker. This allows a health care worker to easily summarize the case for dictation or discussion with others.

A differential diagnosis pane 108 contains the list of possible diagnoses for the patient being evaluated. As each new piece of information or PHI is added to the system, the differential diagnosis is updated.

A menu bar 110 contains menu items that are further described in the section Menu Structure herein below.

In one format, the disease object window can be open at all times showing one disease object, or, more commonly, it is hidden from view until the heath care giver or patient go into the Vertical Axis of Inquiry (VAI)

An interview pane (not shown) presents questions directly to the user individually with a preamble that defines the question.

In addition, there are several "pop up" windows that are context dependent. These include the following:
- Gantt input control
- Disease reference list
- World geographic reference
- Work up pane
- Onset time-shape
- Slider tabs
- Nexus point window
- Symptom watch window
- Topographic avatar Section II: The Consultation A. Sensitivity Levels The consultation tab sets the general parameters for the upcoming patient consultation. Variables for the consultation include the "sensitivity" level of the consultation, which describes how thorough the consultation will be. There are five levels of sensitivity.

1. The First Level of Sensitivity

At the first level (which is also the default level) all of the diseases encountered in emergency medicine and primary care are included in the run time database. For a disease to be included in the first level of sensitivity, it has a specified degree of at least one of three properties: urgency, seriousness, or high prevalence in the population from which the patient comes.

"Urgent" diseases are those in which an immediate diagnosis is critical for preserving the window of opportunity for therapeutic intervention. Examples of urgent diseases are acute coronary syndrome (ACS), myocardial infarction, or heart attack. These diseases are diagnosed as quickly as possible to allow for proper life-saving treatment.

"Serious" diseases have a longer time frame for diagnosis, therefore are considered serious but not urgent. An example of a serious but not urgent disease is a patient whose headache is caused by intra-cranial pressure, which in turn is caused by a brain tumor. This is to be diagnosed; however, the degree of urgency is less than that of a diagnosis of subarachnoid hemorrhage.

2. The Second Level of Sensitivity

A second level of sensitivity adds a set of disease defined generally by a medical specialty. Referring to FIG. 2, an Anatomic system—Cause two-dimensional array is used to quickly select the field of interest. Shown below, each disease is represented by a given cause of disease acting on an anatomic system of the body.

The column headings 200 represent anatomic systems of the body and the row headings 202 represent the different causes of diseases. These systems are used in most medical definitions.

In certain embodiments, the anatomic systems are as follows:
- C1—Cardiovascular (heart)
- C2—Cardiovascular (vessels)
- R—Respiratory system
- N—Nervous system
- D1—Digestive system (organs)
- D2—Digestive system (tract)
- U—Reproductive system (male)
- G—Reproductive system (female)
- H—Hematopoietic
- O—Ophthalmologic
- L—Ear, Nose, Throat
- B—Musculoskeletal
- S—Dermatologic
- K—Endocrine
- W—Whole body
- F—Products of conception In certain embodiments, the causes of disease are as follows:
- T—Trauma
- I—Infection or infestation
- A—Allergic or Immune
- P—Poisoning
- E—Environmental
- V—Vascular
- M—Mental
- X—Genetics
- Y—Nutritional/Metabolic/Endocrine
- Z—Oncology
- Q—Whole body At the second level of sensitivity, the diseases that would typically be considered by a specialist are added to the run-time database from which the differential diagnosis is assembled. A subset of diseases can also be added to the differential diagnosis at any point in the evaluation of a patient. For example, if a patient has an eye problem, the user may add the ophthalmologic diagnoses considered by a general opthalmologist at the beginning of the consult.

3. The Third Level of Sensitivity

The third level of sensitivity considers diseases that focus on one specific segment of a specialty. An example would be retinal diseases of the eye.

4. The Fourth Level of Sensitivity

The fourth level of sensitivity includes those diseases that would be handled by a sub-specialty or a regional medical center focusing frequently on one chief complaint. Headache is an example of this sensitivity level.

5. The Fifth Level of Sensitivity

The fifth level of sensitivity considers all the diseases of mankind. This is variously calculated, but, in one embodiment, slightly more than 20,000 diseases are in the MM system database.

B. Sensitivity Factor Set

The consultation can be further customized by the use of the Sensitivity Factor Set (SFS) as defined in U.S. Pat. No. 5,660,176. In general, the SFS refers to the many variable thresholds in the systems which are used to establish the probability of diagnosis.

In one embodiment of the MM system, the SFS set is accompanied by a "slider" control consisting of an analog scale from 0 to 100. A setting of 100 would make it relatively "easy" for a disease to be considered and ruled in as a possible diagnosis.

This is accomplished by altering the scalar thresholds that are use to give different weights to different levels of a PHI. For example, various degrees of fever have a sliding scale of weights.

The more sensitive the system, the more new diagnostic possibilities are added to the differential list with each new PHI that is established. Generally, the differential diagnosis is assembled based on the initial input of PHIs including those selected by the patient as "key" or "clue" words, and the presenting chief complaint set selected by the user.

When a PHI is established that is found in a disease that is not in the differential list, and the sensitivity of the system in increased, it will be added to the differential. The more sensitive the system, the longer new disease possibilities will be added to the differential.

There is always a trade off between sensitivity and specificity, in regards to the amount of time to interact with the system. A more sensitive or "careful" system utilizes many more questions to be asked.

C. Scope of Inquiry

A third way of customizing the consultation is the use of the Scope of Inquiry (SOI) function. This refers to what the system does with pieces of information that do not match the disease that has been diagnosed. This is analogous to the review of systems (ROS) in a diagnostic evaluation performed by a doctor. The doctor will ask questions about each organ system of the body, even if not related to the patient's problem. If these symptoms are not found in the diagnosed disease, and if they are not found in the patients previously diagnosed diseases, they are "set aside" and dealt with at the end of the consultation. The SOI setting tells the MM system how aggressive to be with any unrelated complaints.

D. Time Context

A fourth way of customizing the MM system regards the use of time. The time context refers to the extent the MM system will consider time during the patient's consultation. A disease "declares" itself by how it unfolds through time, such as the sequence and patterns of the symptoms, the onset characteristics of each PHI and the way in which PHIs vary with time.

Thus, the use of time allows a disease to be more accurately diagnosed, and also to be diagnosed at the earliest point in time. Again, though, there is a tradeoff because of the time it takes to establish the absolute or relative onset times of all of the PHIs, how long each lasted, and the offset characteristics (e.g., sudden or gradual), etc.

E. Diagnostic Ranking Formulas

Figure 9:
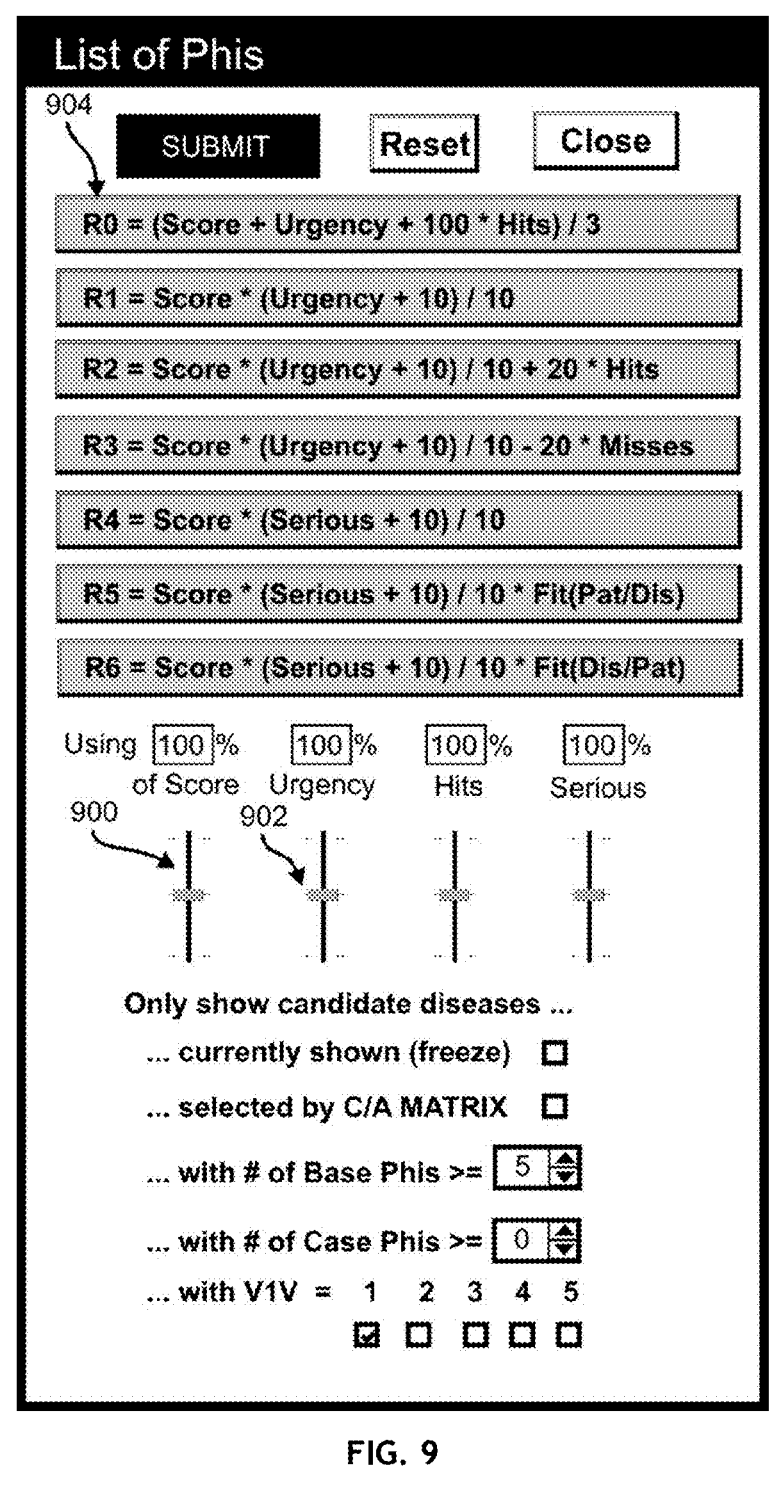

Referring to FIG. 9, the matrix system has several different methodologies that are used in several ranking formulas 904. Several methodologies are described in U.S. patent application Ser. No. 10/846,165, entitled Panel Diagnostic Method and System, which is hereby incorporated by reference.

The ranking formulas 904 are actually customizable by the user. In addition, the contribution of each of the aspects that are used in the ranking formula, for instance Percent of Score 900 and Urgency 902, can be changed.

Section III. Data Input

The data input system is designed to allow the user to enter in specific kinds of information with the fewest possible keystrokes or mouse clicks. Input is generally sequenced similar to a diagnostic to facilitate a smooth flow through the data input system.

A. Population Tab

To be accurate, differential diagnoses should be "population" specific. That is, basic pieces of demographic information can radically change the diseases to be considered in the upcoming evaluation. Referring to FIG. 3, the most obvious examples are age 300 and sex 302. In addition, the patient's race 304 and certain geographic information 306 can be very helpful estimating the probability of certain diseases.

The population tab allows the following information to be input:
  Sex of the patient
  Age, Age group, or Date of birth
  Race
  Geographic information.

B. Special Population Tab

There are certain subsets of patients that share features such that there is a difference in the diseases that one might expect to find for a given set of presenting symptoms. This tab allows the user to quickly indicate if a patient is in one of these subsets. Examples of special populations are as follows:
  Pregnant patients
  Neonates
  AIDS patients
  Intravenous drug users
  Alcoholics
  Patients with cancer
  And other special populations.

C. Time Tab

The time tabs seeks information about time context of the patient's illness. Specifically, the time tab looks to know whether the patient is still suffering from the complaints that prompted medical attention, or if the symptoms have gone away.

In addition, the duration of patient's illness is generally very important because many diseases can be excluded from diagnostic consideration due to this fact alone.

D. "Key Words" Tab

Figure 4:
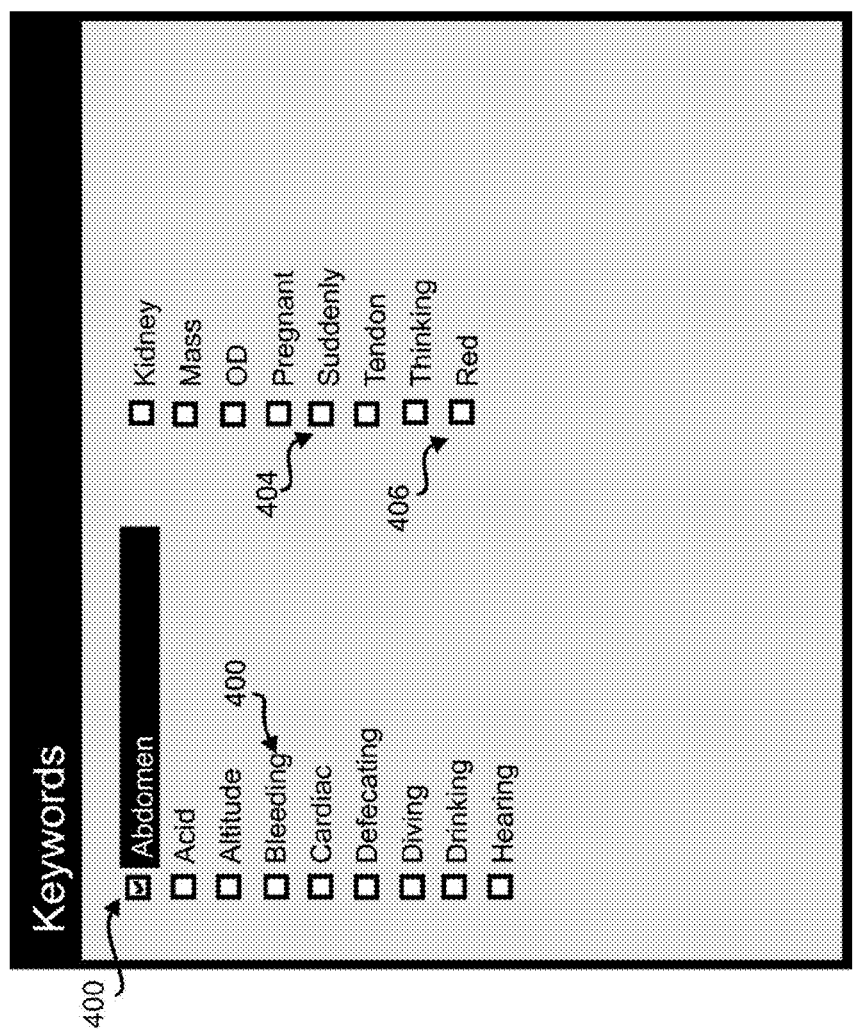
FIG. 4 is an exemplary screen display of an embodiment of a key words input panel used by the GUI.

Referring to FIG. 4, "Key" or clue words refer to the words that a patient or layperson might use to describe their symptoms. In certain embodiments, all diseases are indexed with these words and a differential diagnosis can be assembled based upon these alone. A key word can be a Symptom 400, an Anatomic area 402, a Descriptor such as "suddenly" 404 or even a Color 406.

E. Vital Sign Tab

Vital signs can be quickly entered in the vital sign tab. These can either be expressed as ranges or by the precise value. Most vital sign abnormalities (e.g. fever, hypotension) are also shown in the chief complaint set tab.

F. Chief Complaint Set Tab

Referring to FIG. 5, a chief complaints tab shows a list of common symptoms that are matched to the list of the patient's presenting illness. These symptoms/signs can be sorted by various criteria, such as alphabetical, by anatomic system or cause, or by the affected topographical area on the patient's body. Clicking on the Avatar (not shown) and then selecting from the nested menus can also obtain the presenting symptom set.

The chief complaints are linked to the "key" words. All diseases considered by MM are indexed by both the chief complaint and by the "key" words, and each word is weighted differently in each disease.

G. Matrix Tab

As discussed earlier, the anatomic-cause matrix, such as shown in FIG. 6, is used to select subsets of diseases to be considered by the diagnostic engine. In addition to selecting an entire column (anatomic system) 600 or an entire row (each a cause of disease) 602, the user may click in the cell defined by the intersection of the above. This selects a further subset of diseases. For example, a user clicks on the cell coordinates defined by the two letters "R" (respiratory system) and "I" (infection/infestation) as shown at label 604. This identifies a subset of diseases caused by bacteria, viruses, Chlamydia, prions, parasites, etc. that affect the respiratory system, e.g., nose, trachea, bronchi, lungs, etc.

In certain embodiments, a single click will select a subset of diseases; while a double click causes that cell to "explode". When a specific cell is pinpointed, that cell "explodes" or expands to reveal a nested two-dimensional array. In this display, the columns consist of subsets of the anatomic systems involved, and the rows consist of subsets of the causes of disease. To continue the example given above, the user may select a now nested cell defining viral disease of the bronchioles such as bronchiolitis in a child. The list of diseases added can be unfiltered by the PHIs already established at the time the matrix tab is invoked. The matrix tab may be used at any point in the consultation.

H. PHI Matrix Tab

Figure 12:
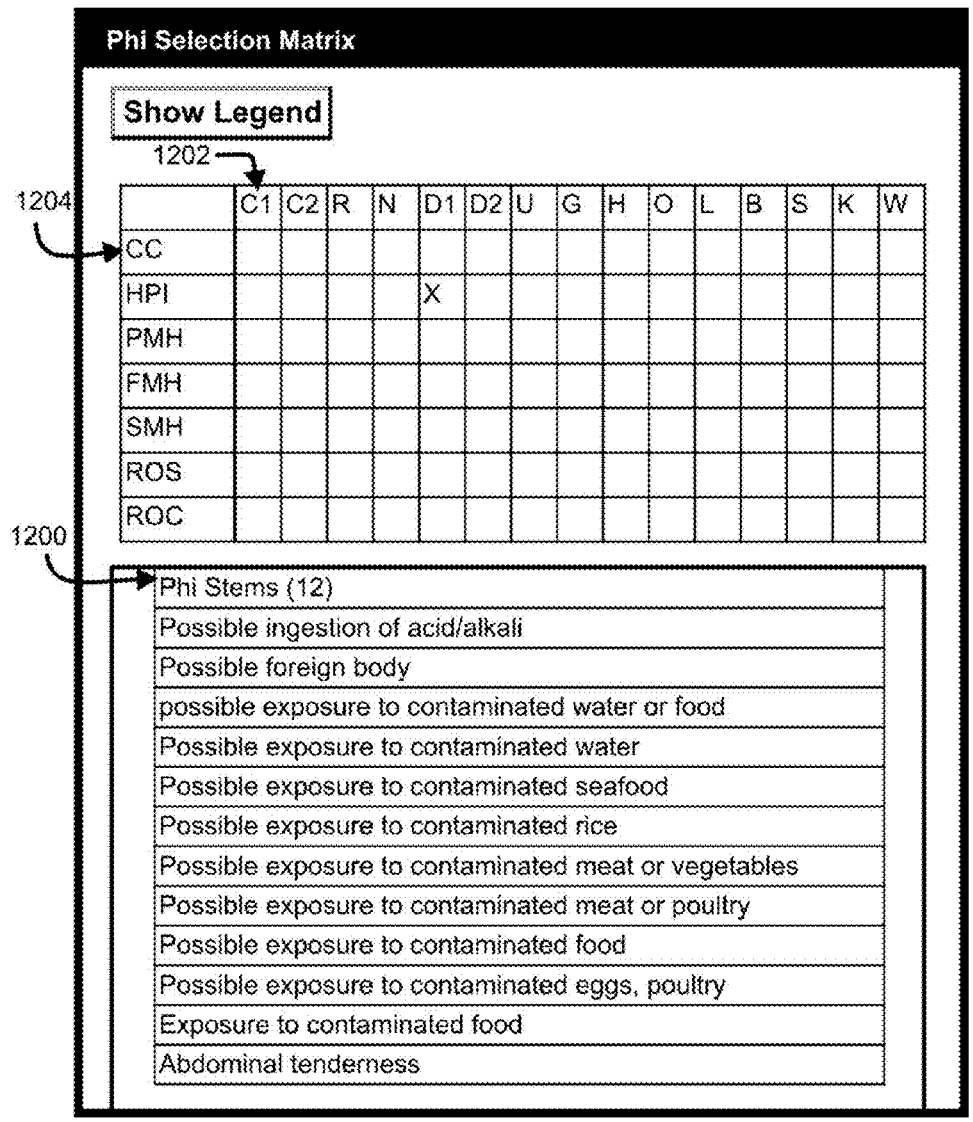
FIG. 12 is an exemplary screen display of an embodiment of a PHI selection matrix panel used by the GUI.

Referring to FIG. 12, in the PHI matrix tab, top level or "Stem" PHIs 1200 can be quickly selected by identifying their respective anatomy 1202 and/or part of workup 1204. The shown workups 1204 are a subset of possible workups. The acronyms for the workups shown in FIG. 12 and other possible workups are as follows:

CC=Chief Complaint
HPI=History of Present Illness
PMH=Past Medical History
ROC=Review of Causes
ROS=Review of Systems
SH=Social History
FMH=Family Medical History
VS=Vital Signs
SMH=Social Medical History As with the previous matrix, the user may select an individual cell 1206, combination of cells, or they may opt to select an entire row or column. A benefit of the matrix is to allow the user to very quickly locate and provide an answer to any PHI in the system.

I. Mimics Tab

The mimics tab provides a detailed analysis of a selected disease as compared to other diseases that may have similar presentations. This feature allows a user to identify specific differences or wedge questions, which may help to distinguish one disease from other possible causes of the presenting PHIs.

Section IV: Work Up Progress

If the functions of the MM system are being used in the typical temporal sequence, by this time, the population specific data and the patient's presenting chief complaint set have been input and the system has established a population and a patient specific differential diagnosis.

To use the auditorium metaphor, at this point, we would have assembled a number of world-class disease specific specialists specifically to solve this case. It is here that each expert begins voting for what question he or she wants answered. The list-based processor here considers the diseases in deliberation, what is known about the patient and the relative urgency, seriousness and prevalence of the diseases in diagnostic consideration to dynamically assemble or sequence the questions.

In the MDATA system, and in the interview mode of the MM system, the questions are presented sequentially to the patient in simple language with a preamble which describes and defines the information the question is asking about.

In the MM system, these questions can be presented to the user in "batch" mode in a series of tabs called the Horizontal Axis of Inquiry tabs.

A. Horizontal Axis of Inquiry Tabs

The MDATA diagnostic engine runs in two modes, the first one being the horizontal axis of inquiry (HAI), and the second one being vertical axis of inquiry (VAI). In HAI, the most likely disease is not yet established, so questions pertaining to several diseases in the differential diagnosis are asked. When a patient indicates that a certain PHI is present, the disease specific diagnostic weight of that question is added to each respective disease object.

Each expert "listens" to all of the questions being asked. When the patient answers, the new information will make each disease either more likely, less likely, or its probability will not change.

Referring to FIG. 7, the questions may be presented to the user in batch mode 700. Alternatively, referring to FIG. 8, the questions may be presented to, the user singularly as in the case of interview mode 800.

There are several "formulas" which are used to select the set of questions to be presented to the user or to select the one best question to the patient in interview mode. The formulas usually deal with the number of hits, misses, PHI weights, and PHI "sine" status, urgency, seriousness, and prevalence. As shown in FIG. 9, some of the formulas 904 are modifiable by the user. Methods to select the set of questions to ask may include the sum of weights of the PHIs, prevalence-based selection, formulas such as "100*key word count*urgency/100", or "(hits-misses)*average PHI weight*seriousness/100", and others. These are similar to the various disease ranking formulas discussed earlier. The Vertical Axis of Inquiry (VAI) will be discussed after the case pane is described.

B. Case Pane

Referring again to FIG. 1, the case pane 106 contains all of the information known about the current patient, in certain embodiments. In one embodiment, the default case panel view shows what may be the most important information for the purposes of diagnosis. This is obtained either from the patient's medical record or from the diagnostic evaluation. Generally, the most important pieces of population specific information may include age, sex, race, geographical information, and whether the patient is in a "special" population group that could significantly alter the diagnostic possibilities.

In certain embodiments, the case panel 106 shows the PHIs that the patient has (in green), the PHIs the patient has denied (in red), and the PHIs the patient is unsure of (in white). If the medical record is available, it can also contain a list of the patient's current diagnoses.

C. Differential Diagnosis Pane

Referring to pane 108 of FIG. 1, the list of possible diagnoses is positioned to the left side of the pane, followed by a series of column headers which can be customized by the user. Exemplary pane 108 shows one possible arrangement, where R0 through R6 are different ranking formulas. These formulas are customizable and may include Bayesian probabilities, allowing the importance of the individual components of the ranking scores to be varied. This can be seen in FIG. 9 which is the Candidates tab seen on the main screen of FIG. 1.

Continuing from left to right, in pane 108 of FIG. 1, Score is heading for a base sum of the diagnostic weights, unmodified by any of the ranking formula components.

"Urg" is a heading for urgency of the disease. In certain embodiments, this is a five point scale from 5, the most urgent to 1, the least urgent.

"Ser" is a heading for Seriousness of the disease. This too is a five point scale with 5 being the most serious and 1 being the least serious.

"Prev" is a heading for the prevalence of the disease. In this view of the prevalence, the absolute prevalence, e.g., the number of patients with the disease per 100,000 of the population of North America per year, is replaced by a 10 point scale with 10 being the most prevalent and 1 being the least prevalent.

"Hits" is a heading for the number of PHIs that match each disease.

"Mis" is a heading for the number of misses, that is, the number of PHIs that the patient has that do not occur in each disease.

"Epid" is a heading for epidemic watch. This is an attribute of any diseases that could be seen in an epidemic. This is a Boolean value, e.g., 1 for yes, 0 for no.

"W" is a heading for weapons of mass destruction (WMD). This is an attribute of any disease that could be seen as the results of a weapon of mass destruction.

"W2" (the "2" is cut off and not shown in FIG. 1) is a heading for the type of WMD threat as follows: "B" is biological, "C" is chemical, and "N" is nuclear.

"R2" (CG cut off) is a heading for "Risk to Caregiver". This is an attribute of any disease that could pose a significant risk to the caregiver. This is typically an infectious disease.

"D" (M cut off) is a heading for "Don't Miss. This is an attribute of the diseases which one "does not want to miss", that is, a disease that must be excluded from diagnostic consideration before another disease is thought to be the diagnosis.

Each of these columns can be used to sort the differential diagnostic table.

D. Focused or Segregated Differential Diagnosis Pane

The second phase of the diagnostic process is optional and many times not necessary. Frequently, as the care give reviews the differential diagnosis, it is possible to narrow the possibilities to five or fewer diseases. As mentioned briefly above, if the user elects to select the most likely candidates from the differential diagnosis and concentrate on those diseases, the user simply clicks in the "focus" column of diseases of interest in the differential diagnosis pane and clicks "segregate". This will cause a sub-window to open containing only the selected diseases. At this point the HAI tabs will show questions taken from only the disease objects in the focused subset. As always, however, all diseases in the differential will continue to be weighted.

E. Sub-PHI Analysis

Each PHI in the system is a part of an inverted tree with the most general PHI being the root. For example, a tree may be as follows with the root being listed first: abdominal pain—right lower quadrant—colicky.

In addition, PHIs are modified and indexed by the N-dimensional array that constitutes a Timed Descriptor Spectra (TDS). These attributes include severity of pain, time shape of the onset, quality of pain, what precipitates it, and what makes it better. These help clinicians to more precisely define a symptom and are generally very important in diagnosis.

These attributes are shown to the user in the VAI mode in the disease object pane. But there are times when it is these attributes which allow a distinction to be made between several very similar disease processes. When the user has used the segregated disease or disease focus feature, these attributes are "visible" and are included in the HAI suggested questions. In addition to the TDS spectra attributes, a Gantt input pop up window is also available in the segregated disease analysis pane.

F. Disease Object Pane

Referring to FIG. 10, an exemplary embodiment of a disease object panel is shown which contains all of the information relating to one disease. This panel is either invoked or shown when a disease name in the differential tab 108 (FIG. 1) is selected.

The disease object panel itself has a set of tabs nested inside it. The default view of the disease object is the one used by the clinician in the vertical axis of inquiry (VAI). The VAI is the mode of operation used when the diagnostic engine is focusing on a single diagnosis. At the same time, all of the PHIs that also occur in other disease objects are being weighted as they are established.

The default VAI tab shows all of the symptoms, signs and vital signs listed on the left side of the tab. In certain embodiments, all PHIs already established in the patient are shown in green, all PHIs denied are in red, and all unknown are in white. Therefore, the clinician can very easily see the PHIs that are to be evaluated to establish the diagnosis.

The value of each PHI and its associated weight is shown so that the clinician can generally concentrate on the most important PHIs first. There are several other sorting criteria that the clinician can use. Any PHI can be clicked on and it will open the PHI object. The PHI object shows all the diseases in which that PHI is present. This is a kind of instant differential diagnosis. Any disease may be selected and "opened" by clicking. In every disease object, in certain embodiments, the PHIs that match the disease are shown in green. Those that do not are shown in red. The weights of all of the PHIs in the disease object that is open are also displayed.

G. Disease Relationship Tab

The disease relationship tab displays a graphical representation of all of the risk factors, complications, and associated diseases that are related to the current disease. Risk factors and conditions that cause the disease are shown to the left. The differential diagnoses of this disease or the diseases that may present in a similar manner are listed directly under the diseases. Diseases that the current disease may cause or complications of this disease are shown to the right.

The relationships between the diseases are represented by a commonly used Java applet that allows the relationships to "fall into their natural position" after the graph is perturbed. (See The Visual Thesaurus® from Thinkmap, Inc. for example).

H. Disease Summary Tab

This tab contains a text summary of the disease.

I. Geographic Tab

The geographic tab has a world map in which the prevalence of the diseases is represented by different colors.

J. Single Disease Work Up Tab

A "work up" is defined as the tests (laboratory, imaging, and special tests like EKG) that are used in addition to history and physical examination to help establish the diagnosis.

In the Disease Object pane, the work up tab shows the current best laboratory test(s) of choice, the imaging modality of choice and special studies of choice to establish the diagnosis of that disease.

There are times when a clinician has limited the differential down to a small number of diseases by history and physical examination, but needs the better diagnostic resolution provided by addition testing.

In this case, the user can invoke the global work up function. This functions as follows. The clinician selects several possible diseases from the differential diagnosis and then selects the global workup function. This function retrieves the lab tests of choice, imaging modality of choice and special studies of choice for the disease selected. Then it deletes duplicates and displays the results to the user.

K. Disease Object Feedback Tab

By choosing the disease object feedback tab, the user can give their input on what disease object information may need modification, additions or corrections.

L. Disease—PHI "Surfing"

Again, in the disease object, a left click on any PHI will instantly open the PHI object in which all of the diseases that contain that PHI are listed. Any disease may be selected by clicking and that disease object is opened. The PHIs that the patient has are colored green and the PHIs that do not match the disease are colored red.

M. Central Feedback

The MM system can be linked to a central web site to exchange data about possible WMD (Weapons of Mass Destruction) or possible epidemics. This link can also facilitate the exchange of data regarding new treatments of choice or information regarding new tests of choice.

Section V: The Interview Mode

Figure 8:
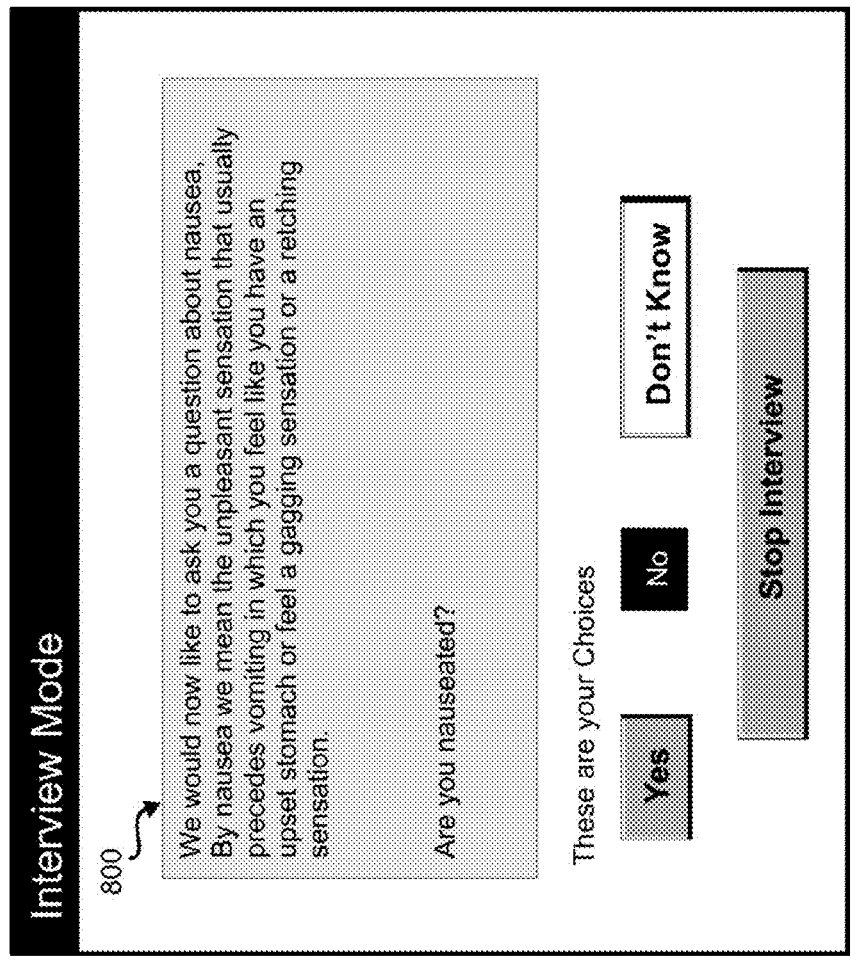
FIG. 8 is an exemplary screen display of an embodiment of an interview mode response to question (for PHIs) input panel used by the GUI.

The MM system can be run in a fully automated mode, which in the MM system is referred to as the interview mode (IM), such as shown in FIG. 8. In this case, the system functions as the fully automated MDATA system. It assumes there will be no outside human intervention until the end of the consultation, or none at all.

There are three differences in the way in which questions are presented in the IM of the MM system. First, the questions are presented one at a time, sequenced by the list-based or diagnostic engine based on the "votes" by the disease objects. Second, each question is preceded by a preamble or introduction that precisely defines the information that is being requested of the patient. Finally, the language used is very basic and is intended for someone with no medical background. Specific aspects of the questions, like the language used, the sophistication of the language can be controlled by the "Question Roller" function discussed in U.S. Pat. No. 6,234,964, which is hereby incorporated by reference.

In IM, the patient may be requested to perform a physical self-examination, which may call for the assistance of another person. This person does not need to be medically trained to assist in the examination, as the IM will list step-by-step instructions in non-medical terms. Thus, the provisional diagnosis is based solely on a patient's medical history and physical self-examination.

Section VI: other Pop-Up Data Entry Windows

A. Gantt Input Control

As previously mentioned, in general, one of the most important factors in determining a correct diagnosis may be to consider the timing of the onset of the patient's symptoms. A Gantt chart is a horizontal bar chart developed for use as a production control tool. In certain embodiments, the MM system contains a Gantt chart which displays all of the patient's symptoms in order of appearance. These symptoms are displayed as horizontal bars which can be rearranged to match the onset sequence of the patient's illness. This information is then interpreted by the MM system and the diseases that most closely match this pattern are given extra diagnostic weight.

B. Graphic Input of Onset and Other Time Shapes

Generally, the onset "time shape" of a symptom may be very important. For example, the sudden onset of a pain suggests a vascular or colic event. A discontinuous onset (i.e., a symptom that occurs and then stops then reoccurs) is also frequently a vascular problem. For example, angina pectoris, pain from the heart caused by insufficient oxygenated blood, often "stutters" in its onset.

Onset types include exponential onset, linear, and sinusoidal. Each has clinical significance.

In order to quickly indicate the onset characteristics of a PHI, a simple graphic input window opens and the user or patient may indicate the time shape of the onset of the symptoms by the way they vary through time and their offset. A Runge curve fitting algorithm is used to transform the shape input for the user to several suggested forms.

Several other time shapes are generally important in diagnosis. For example, when the severity of pain through time plots a sinusoidal curve, frequently a cylindrically shaped structure is obstructed. Renal colic, biliary colic, crampy abdominal pain of small bowel obstruction and pain of labor are examples.

Onset and offset analysis is accomplished by another input popup window which plots the severity of a symptom through time. Analysis of offset time shapes and onset of symmetry are supported as well as all of the patient's symptoms considered together.

C. Nexus Point Action Plateau and Symptom Watch Window

In the MDATA system, the Nexus Point (NP) is defined as that time in a patient's illness when the symptoms seemed to have "turned the corner" and begin to improve. Generally, this is an important point because, frequently, if the patient is improving on their own, further workup is deferred to allow "nature to affect the cure" as Sir William Osler recommends.

There is a small window that contains "meta" information about the consultation. Included in this input area is a place for the patient to indicate if he believes he may be beginning to improve.

The MDATA system also provides an "Action Plateau" (AP) feature which warns the patient that a dangerous situation has been reached, and even taking the time to continue the current consultation could be detrimental. The same function is present in the MM system. The use of a simple graphic "risk thermometer" warns the patient and/or physician of a potentially dangerous situation for the patient, the care giver, or both.

During a consultation, particularly in a fully time-based one, the appearance of certain symptoms can change the actions that are to be taken. The example of appendicitis will be used to explain the principle. A patient that has anorexia, and poorly localized epigastric abdominal pain with nausea and/or vomiting may have early appendicitis. In appendicitis, the Diagnostic Point Symptom (DPS) is the movement of this pain into the right lower quadrant of the abdomen. When this occurs, there is a significant increase in the probability that the patient does have appendicitis, even before RLQ tenderness or rebound tenderness develops. The Symptom Watch (SW) function allows immediate action to be taken as soon as the DPS occurs. The SW window has a list of symptoms that the patient is instructed to click on if any of these symptoms occur during the interview mode.

D. Alternative Input Tabs

Typically, the patient describes several symptoms which are used to retrieve diseases to formulate the differential diagnosis. These disease objects are then used as the basis for enquiring about other symptoms, signs, etc.

There is an alternative way for the patient or caregiver to enter data into the system. The evaluation may be approached from a traditional doctor-patient interaction through a series of nested outlines or matrices.

The MM system can follow the traditional input sequence of information allowing the user to first enter the chief complaint set, history of the present illness, review of systems, past medical history, family medical history, social history, vital signs and physical examination findings. In the same way that each PHI is really an inverted tree, in certain embodiments, so are the other PHIs structured and presented to the user. For example, each symptom starts from the anatomic system involved. Then the past medical history, family history and social history are structured. The same is true for physical examination maneuvers.

E. All Slider Tabs

The process of varying one parameter in a clinical case can be very helpful in the diagnostic process. For example, if the age of patient is varied, the differential diagnosis will change depending upon the age. This is somewhat analogous to a "sensitivity analysis" in accounting. The slider controls allow the following parameters to be dynamically changed Age
Sex
Duration of Symptoms
Geography
Vital signs
Duration of PHIs F. Multiple Disease Work Up Tab Again, in the same way that a user can look up the tests utilized to confirm one diagnosis in a disease object's work up tab, there are times when several diagnostic possibilities are still under serious consideration and a testing plan is to be created to distinguish between the various possibilities.

The multiple disease work up tab accomplishes this. Any set of possible diagnoses can be selected, and the work up function invoked, which will cause a testing plan (usually expressed as an algorithm) to be displayed in the work up tab. This is most frequently used when a final set of diagnoses is being considered in the segregated or focused disease set.

G. Panic Tab

There are certain standardized ways of handling very critical situations in medicine. The most easily understood examples are Advanced Cardiac Life Support (ACLS) and Cardio Pulmonary Resuscitation (CPR). In each case, very specific steps, procedures, and medications are indicated. They are usually committed to memory because there is not sufficient time to look up information in these time-critical situations.

The Panic tab has instructions for the Heimlich Hug, CPR and ACLS available with one or two clicks in the MM system. The contents are actually kept in the treatment tables so they can be updated as often as necessary.

H. Reports Tab

Due to the fact that all questions asked and answered have a time and date stamp, the system can prepare a detailed report for both patients and caregivers. The standard MDATA report contains the following information:

The differential diagnosis of the considered diseases
Any diseases that cause the patient's symptoms but were ruled out
A time and date stamped history of the diagnostic evaluation
A reference section including the following for the top three diagnostic possibilities:
Laboratory test of choice for the top three diagnoses
Imaging modality of choice for the top three diagnoses
Special study of choice for the top three diagnoses
Treatment of choice for the top three diagnoses.

Figure 11:
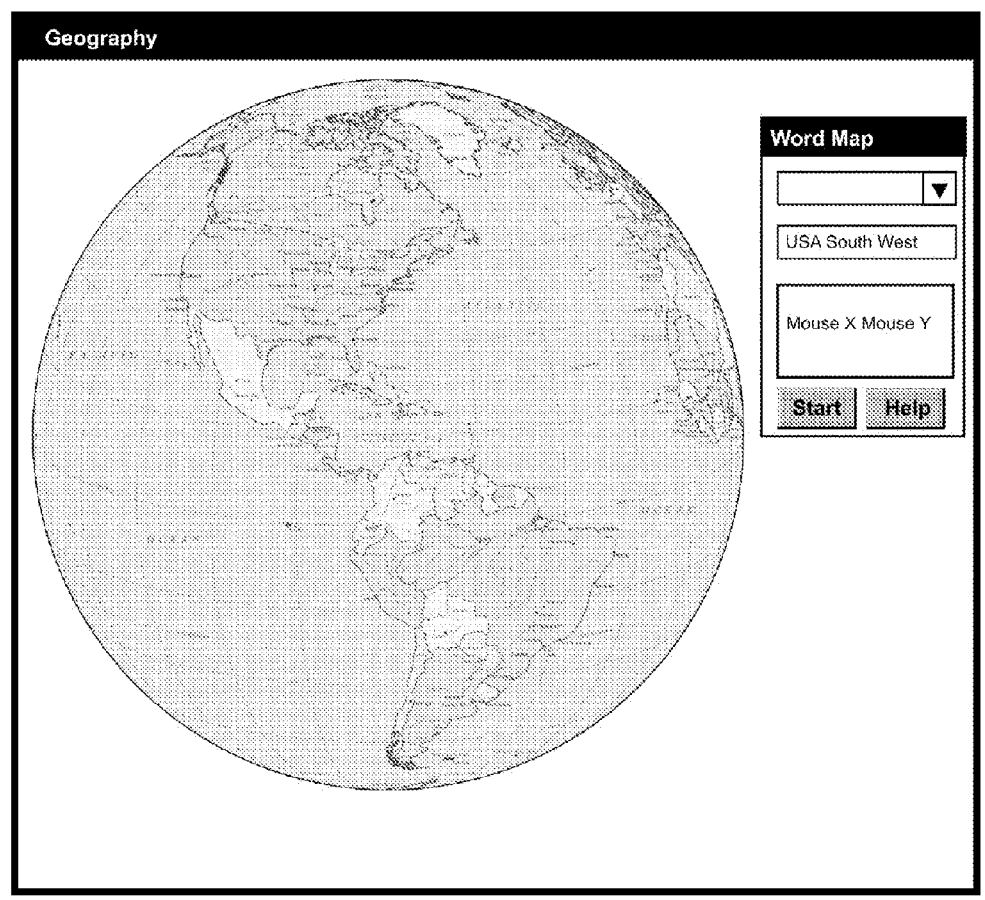
FIG. 11 is an exemplary screen display of an embodiment of a geographic specific information panel used by the GUI.

This information, plus any geographic-specific information, as shown in FIG. 11, is also available on the MM system. FIG. 11 is an input panel where the user is able to quickly enter geographic locations such as country of birth, recently visited countries, and/or current geographic location in a graphical manner. Of course, other reports showing other information, including a different number of top diagnoses, can be prepared by the system.

Section VII: Update and Feedback Functions

A. Update Functions

As in the MDATA system, the users are in partnership with the entity maintaining the system to constantly improve and expand the system. The MM system is a constantly evolving system. Generally, an important part of this involves the update and feedback loops built into the system. As new tests, imaging modalities and treatments become available, the MM system is updated when it is connected to the website of the entity maintaining the system.

In certain embodiments, the following aspects of the MM system are updated:

Changes to the application or executable files
Updated lab tests, imaging modalities and treatments
New or modified disease objects
PHI weights.

B. The MM Feedback Functions

In addition to downloading of information, important feedback information to monitor and improve the system is uploaded whenever the MM system application connects to the website of the entity maintaining the system.

Feedback information from the MM systems to the website includes the following information:

"Final" diagnosis for each case
Case PHIs associated with the final diagnosis
Epidemic watch information
Possible WMD information
Other.

It is often said that there is no substitute for experience. Expert clinicians refine their diagnostic skill over time by comparing their patients' symptoms to both what they thought was the diagnosis to the "final" diagnosis. This process is not only reproducible but the experience of many clinicians can be pooled, and what is learned quickly translated into better diagnostic weights and a more accurate and useful system.

In order to accomplish this, a system based on continuous feedback, analysis and modification has been created. User feedback allows the entity maintaining the system to alter such parameters as the diagnostic weights through time to be more accurate. Currently, there are no universally accepted diagnostic weights of PHIs. This is particularly true when the diagnostic weight of a PHI changes depending upon the disease timeline.

The MM system is based primarily on history, physical examination findings, and vital signs, such as pulse and temperature. A final diagnosis is usually only possible with an imaging modality (x-ray of a broken bone, CT scan of a sub-arachnoid hemorrhage or a lab test, such as T3, T4 and TSH in hyperthyroidism.) This is why it is generally so important to indicate exactly how the final diagnosis is ascertained.

The idea is to compare what the MM system thought the diagnosis was to what turned out to be the final diagnosis (to the extent it is known under the circumstances of the case.) The user of the system then can designate what the final diagnosis is for each consultation. This is accomplished by completing a check list and a "slider" control, both of which are used to estimate the probability that the "final" diagnosis is accurate.

Diagnoses are considered "final" based on various criteria that are specific to each disease. This information is found in the disease object. Once the clinician enters the final diagnosis into the system, the information is uncoupled from any patient identification information, and sent to the website for analysis. When the information is at the website, the PHIs that were present and their values are compared to the current set of diagnostic weights. This information is then statistically pooled and used to continuously update the weight placed on each PHI.

C. Data Siphon

Data siphon is the function in which the statistical data about the consultation is decoupled from the patient identification information. Each clinical interaction is given a unique code; however, no patient identification information is included in order to protect the patient's right to privacy. Generally, patient anonymity is to be respected. None of the statistical information about diseases can be traced back to a patient's medical record.

D. The Inverse Relationship of Sensitivity and Specificity

There is an inverse relationship between the sensitivity and the specificity of a system. A system with 100% sensitivity (meaning never missing a diagnosis) would have to consider every disease in every patient since any disease could be in the very early phase. A system with 100% selectivity (meaning never diagnosing a disease that was not present) could only achieve this by never diagnosing any disease. Therefore, a balance is set to achieve a balance between these two parameters. The SFS, SOI, and sensitivity "level" are examples of having a "tunable" system.

E. Multiple Stage Diagnosis

In the MM system, the diagnostic process is divided into several stages so that a provisional or clinical diagnosis can be established before testing begins. As stated above, it may not be possible to ascertain the "final" diagnosis until autopsy.

In certain embodiments, the MM system arrives at a provisional diagnosis based on the patient's history, physical examination and available vital signs. After testing is complete, the test results can be added into the MM system. Each test, like each PHI, is weighted differently in each disease. This allows the MM system to significantly increase the probability of making the "final" diagnosis. In addition, this information is generally very important to the feedback system.

F. Other Features

There are several other MDATA features that are incorporated into the MM system. Briefly, they are as follows:

Mental status examination for interview mode

Reenter features

Meta analysis (if patient medical record is available)

Free index feature (use of key words to select candidate diseases)

Avatar input graphic

Risk thermometers

Images and video clips in disease objects

SQL view and functionality of the underlying database

Hierarchical references of all diseases of mankind

Use of a medical record to store the patient's history and use of the system.

Section VIII: General Operating Issues

A. Health Care Giver Mode

Health Care Giver Mode assumes that a caregiver will involved in asking the questions and examining the patient. This mode functions best when there are testing facilities available but generally does not require them.

B. Parsimony Mode

The MM system's default method of diagnosis is based upon the Law of Parsimony. In medical terms, this means that all of the patient's symptoms are being caused by one new disease process.

An Existing Disease Subtraction Layer (EDSL) is used to "subtract" away the patient's underlying complaints due to any other chronic disease(s) in order to establish the efficacy of therapy of the disease being managed. This means that even if some of the patient's symptoms are caused by underlying disease process, the patient is usually able to differentiate different "kinds" of the same symptom. For example, a patient with chronic obstructive pulmonary disease may experience an underlying dyspnea or shortness of breath. This is frequently precipitated by exertion. A patient with left sided congestive heart failure also becomes short of breath but usually when laying flat. This is called orthopnea. It is typically easy for the patient to make this distinction if the correct questions are asked.

In the MM system, the reliance on efficacy of the law of parsimony can be increased by using the EDSL and a carefully constructed and worded history.

C. Negative Weights

The use of "negative" weights can be very helpful in the diagnostic process, but are most valuable when it is assumed that all of the patent's current PHIs are caused by one new pathologic process. Thus they can be problematic, particularly when the patient has underlying concurrent chronic disease processes. The "Existing Disease Subtraction Layer" (EDSL) addresses this issue, by allowing the PHIs of existing diseases to be subtracted from the case. By assuming parsimony, the more PHIs a patient has that do not appear in a given disease, the less likely that disease is to be the diagnosis. The use of negative weights has a built in "synergy" in which the sum of the weight subtracted from each disease is further increased based on the number of non-matching PHIs present.

Another use of negative synergy is when two PHIs actually measure the same pathologic process. For example, in left sided congestive heart failure, paroxysmal nocturnal dyspnea and orthopnea reflect rising pulmonary artery pressure. Thus the combined weight of having both these PHIs present would actually be less than the sum of their diagnostic weights.

In the fully time-based system, not having a PHI that does not occur until the later stages of a disease would tend to increase the probability that the patient is in an early phase of that disease process. For example, not having RLQ abdominal pain makes early appendicitis more likely.

Section IX: Menu Structure

In certain embodiments of the MM system, the main menu structure resembles the standard windows style conventions and consists of a series of nested menus.

The top tier menu structure is as follows:
- File
- Edit
- View
- Insert
- Format
- Tools
- Window
- Help For each item listed above, the following information is the second tier:
- File Menu
  - New
  - Open
  - Close
  - Save
  - Save As
  - Permissions
  - Print
  - Exit
- Edit Menu
  - Copy
  - Cut
  - Paste
  - Find
  - Go To
- View Menu
  - Tabs
  - Case
  - Differential
  - Disease Object
  - SQL
  - Reports
  - Custom Views
  - Full Screen
  - Zoom
- Insert Menu
- Format Menu
  - Font
  - Color
- Tools Menu
  - Redraw
  - Recalculate
  - Interview
  - Show Rank Formulas
  - Drug Dose Calculator
  - Drug—Drug Interactions
  - Central Update
  - Customize
  - Options
- Table Menu
  - Disease table
  - PHI Table
  - Lab Test of Choice Table
  - Imaging Modality of Choice
  - Special Study of Choice
  - Treatment Table
- Window Menu
  - Open Windows
  - Split Window
  - Remove Split
- Help Menu
  - Using the MM
  - MM On Line
  - Check for Updates
  - Report Feedback
  - About the MM.

Section IX: Description of Flowcharts

Figure 13:
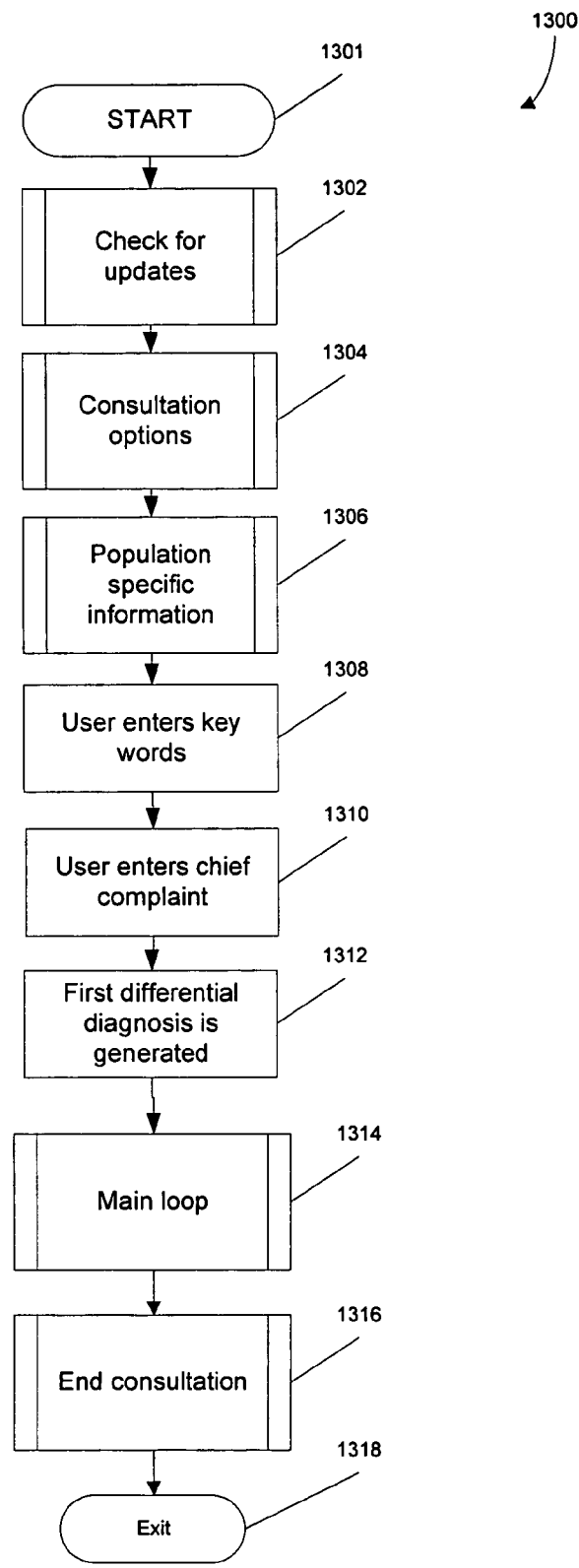
FIG. 13 is an exemplary flowchart of an embodiment of a top level process performed by the Matrix-MDATA system.

Referring to FIG. 13, an MM top level process 1300 begins at start state 1301. The process then checks for any available updates from its master server(s) at process 1302.

Figure 14:
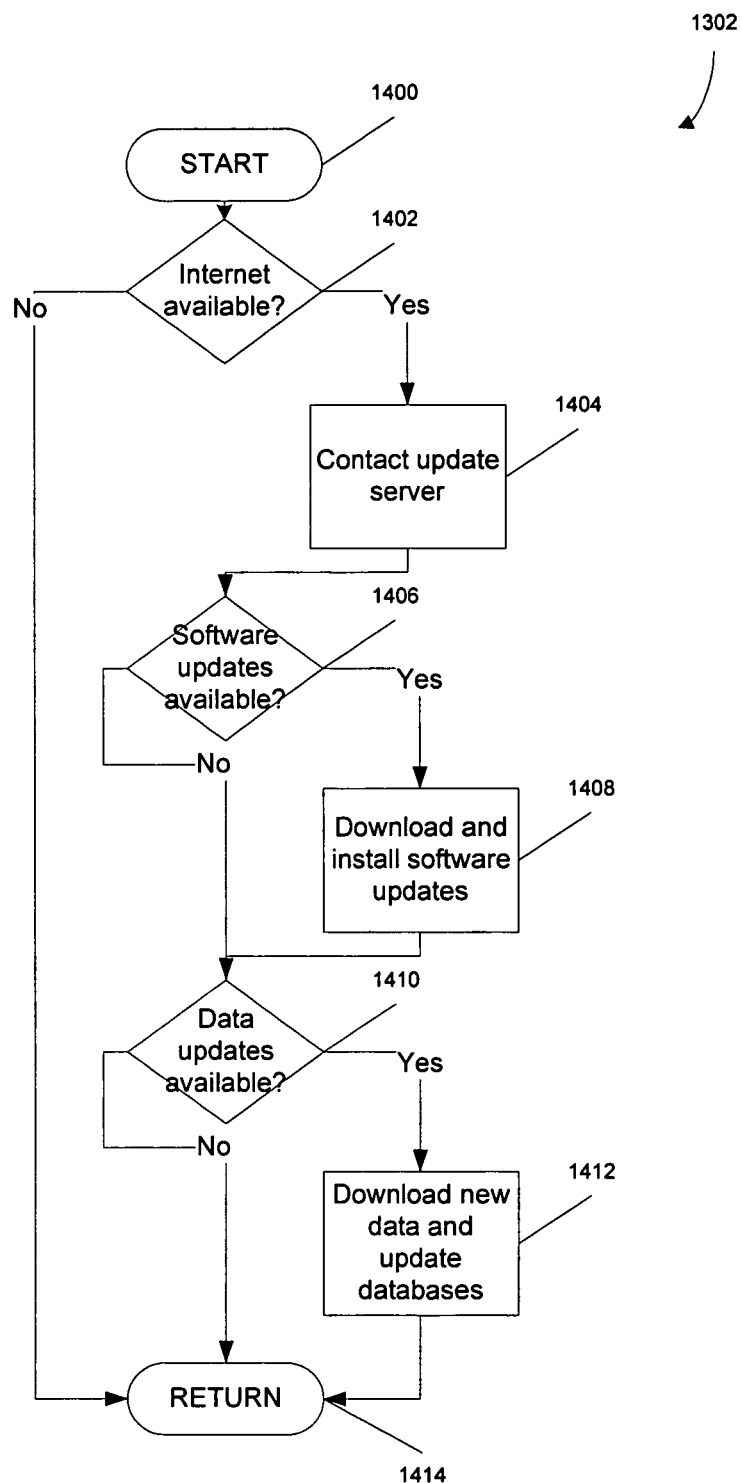
FIG. 14 is an exemplary flowchart of an embodiment of a check for updates process shown in FIG. 13.

Referring to FIG. 14, process 1302 will be described. Process 1302 begins at start state 1400 and moves to decision state 1402 where the availability of a network connection such as an Internet connection is established. If a connection is not available, then the update process 1302 cannot continue and this process ends at return state 1414 by returning control to FIG. 13. If a connection is possible, as determined by decision state 1402, process 1302 advances to state 1404 and makes a connection to an update server. Proceeding to a decision state 1406, process 1302 determines if any software updates are available. If updates are available, process 1302 moves to state 1408 and downloads and installs these updates. Continuing at a decision state 1410, process 1302 determines if any database updates are available. If updates are available, process 1302 advances to state 1412 to download and install these updates. At the completion of state 1412 or if no updates are available, as determined at decision state 1410, process 1302 proceeds to return state 1414 and control then passes back to FIG. 13 at process 1304.

Referring again to FIG. 13, the top level process 1300 continues at process 1304 that allows the user to specify consultation options. These options adjust the scope, thoroughness, and the goal of the consultation. Consultation options are also available to adjust the display style and other options.

Figure 15:
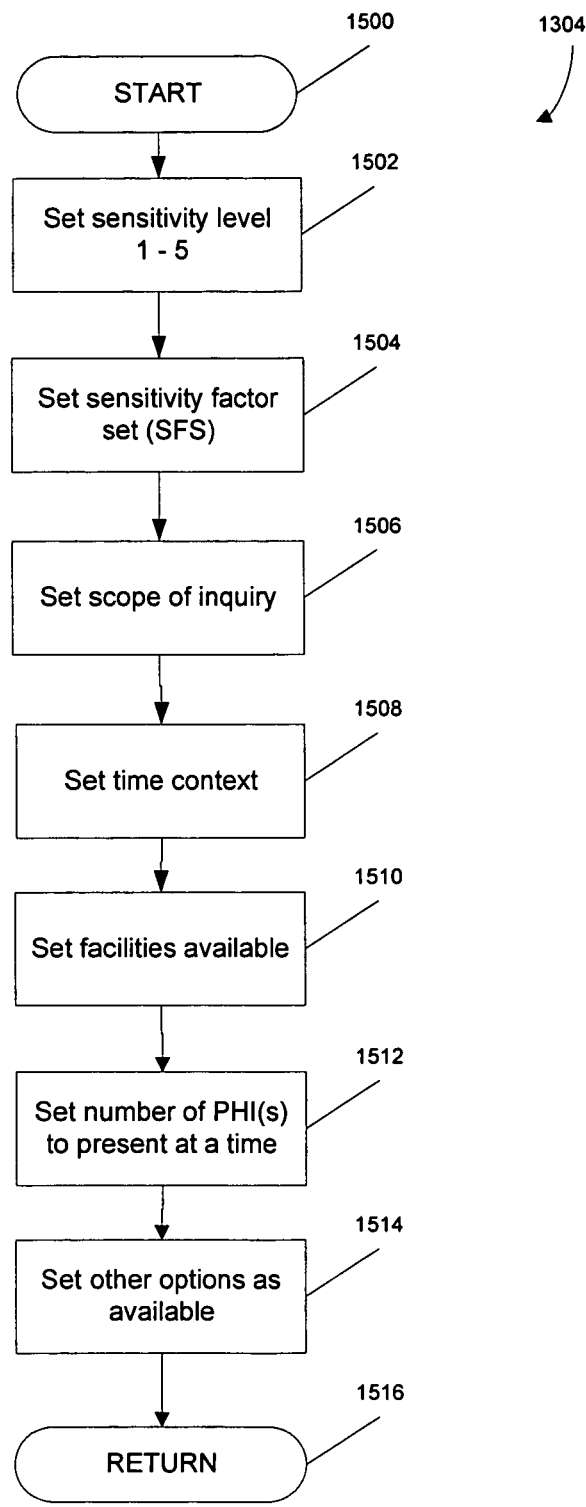
FIG. 15 is an exemplary flowchart of an embodiment of a consultation options process shown in FIG. 13.

Referring to FIG. 15, process 1304 will be described. Process 1304 begins at a start state 1500 and moves to a state 1502 where the sensitivity level of the consultation is selected. The sensitivity level adjusts the number of diseases used throughout the system making the system more or less sensitive as required by the current user. Process 1304 then advances to state 1504 to allow the user to select the SFS (Sensitivity Factor Set). The thresholds in the system are modified by the Sensitivity Factor Set. The default value of the SFS is one (1). This allows all thresholds in the system to be modified without actually altering the system. A table of SFS is kept external to the system. An example would be the Patient SFS. If the patient wants the system to be "extra careful" it would, for example, lower the fever threshold for diagnosing pneumonia. Proceeding to state 1506, the scope of inquiry is selected. This adjusts the system to cater to different levels of diagnostic need. Scope of Inquiry is like the ROS in the medical workup. It determines what the system does with information gleaned from the interview that does not relate directly to the diagnosis. That is, the system investigates the other PHIs that don't fit now, or saves them and comes back to them.

Process 1304 continues at state 1508 where a time context is selected. The time context specifies if this disease process is current and ongoing, in the past, or a hypothetical situation about the possible future. Moving to state 1510, the facilities available are selected. This allows the system to intuitively ask for more advanced findings, only if they are available, such as: EKG reading, X-ray findings, or CAT scan results. Moving to state 1512 the user is asked to specify the number of questions or PHIs they would like presented at one time.

This can be adjusted from interview mode, where a single question is presented directly to the patient, or it can be set to display questions and PHIs in batch mode, allowing faster input of responses by dealing with them as a group. Proceeding to state 1514, the remaining user/consultation options are specified. These include options such as display setting, font usage, and other general options. At the completion of state 1514, process 1304 advances to return state 1516 and control is then returned to FIG. 13.

Referring again to FIG. 13, the top level process 1300 continues at process 1306 to collect population specific information about the patient. This informs the system as to what population the patient may belong to. Items such as age, gender, race, and demographic parameters are often important to the diagnostic process.

Figure 16:
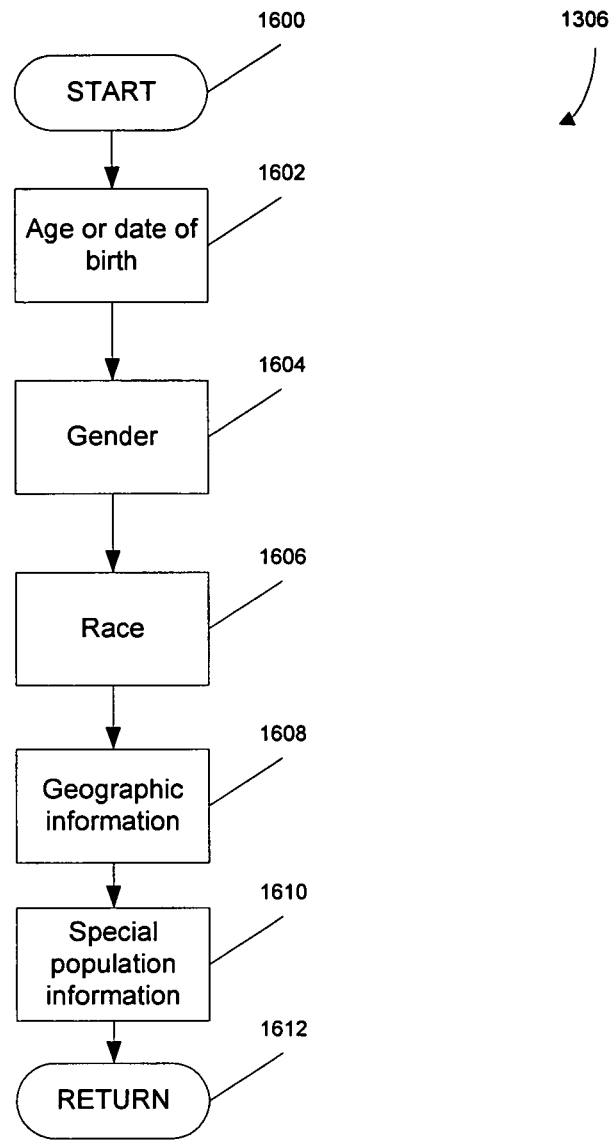
FIG. 16 is an exemplary flowchart of an embodiment of a population specific information process shown in FIG. 13.

Referring to FIG. 16, process 1306 begins at start state 1600 and moves to state 1602 where the age and/or age group of the patient is entered. Moving to process 1604, the gender of the patient is specified and if the patient is female they may be asked to indicate whether or not they believe or know that they are pregnant. Advancing to state 1606, the race of the patient is specified. Proceeding to state 1608, the user is asked to enter any relevant geographic information about the patient. This can include country of birth, recently visited countries and the patient's current geographic location. Continuing at state 1610, the user is asked to select from a list of special populations that this patient may belong to. This can include populations such as IV drug users, HIV/AID patients, pregnant patients, cancer patients and many other possible populations. Once state 1610 completes, process 1306 ends at return state 1612 and returns control to FIG. 13, the top level process.

Referring again to FIG. 13, the top level process 1300 then proceeds to state 1308 where the user is prompted to identify any and all key words that apply to this consultation. Key words are a collection of words that help the system build its initial differential diagnosis. These can be anything from an anatomic region, topographic location, a sense, such as sight, hearing, or feeling, a color, or any number of descriptive adjectives that might apply to the patient.

Moving to state 1310, the user is asked to select from a list of chief complaints that might apply to this consultation. Chief complaints are medically significant signs or symptoms that are used by the system to create its initial differential diagnosis. Advancing to state 1312, the system utilizes all of the information gathered from the user thus far to generate an initial population specific differential diagnosis. This serves as a starting point for the diagnostic process. Process 1300 then advances to main loop process 1314, which is further described in conjunction with FIG. 17.

Figure 17:
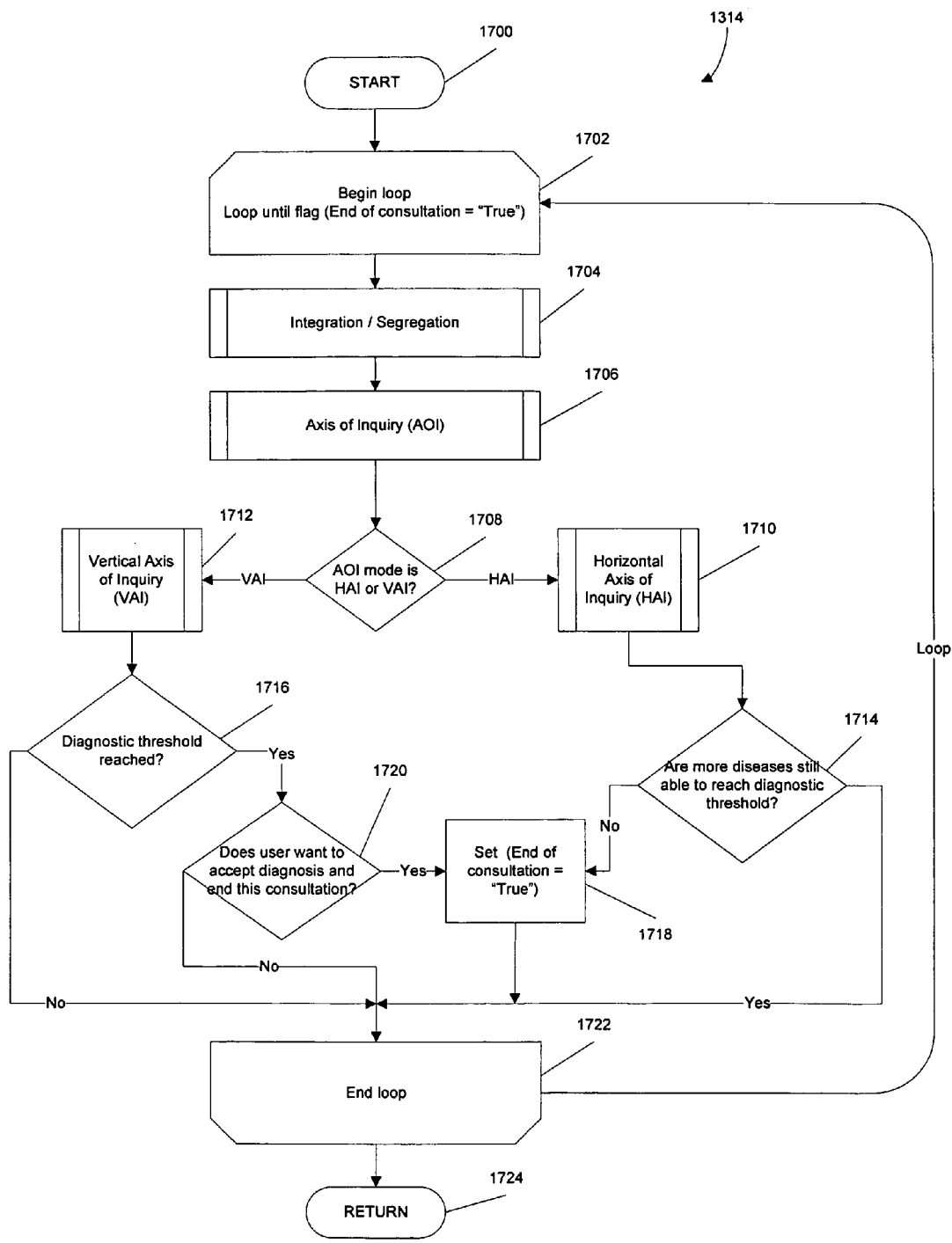
FIG. 17 is an exemplary flowchart of an embodiment of a main loop process shown in FIG. 13.

Referring to FIG. 17, main loop process 1314 begins at start state 1700 and moves to begin loop state 1702. This loop encompasses all of process 1314 from state 1704 through state 1720 and repeats until the system flag (End of Consultation) is changed to true. Moving to an integration/segregation process 1704, the system checks to see if any diseases can be segregated from this consultation or reintegrated into the consultation. This process allows only integrated diseases to vote on the next best PHI to present to the user. Segregated diseases are silent and may only listen to the consultation; they do however continue to be weighted and if their score rises above the segregation/integration threshold, they may be returned to integrated status and thus be allowed to suggest PHIs again.

Figure 18:
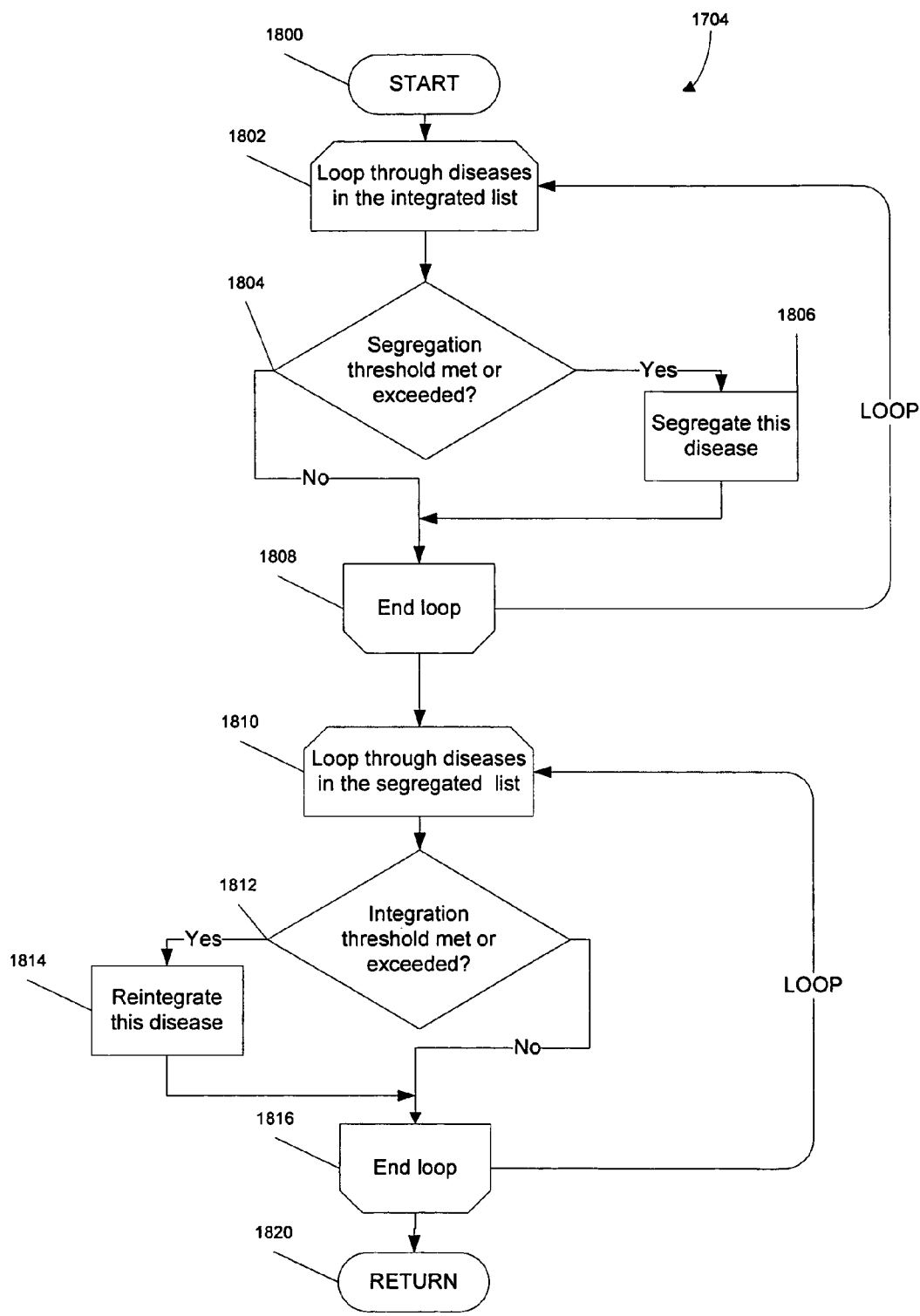
FIG. 18 is an exemplary flowchart of an embodiment of an integration/segregation process shown in FIG. 17.

Integration/segregation process 1704 is described in FIG. 18 where the process begins at start state 1800. Moving to state 1802, a first loop begins where each disease in the integrated disease list is tested once at a decision state 1804. Here each disease's threshold is evaluated, and if it meets or exceeds the segregation threshold, it is moved to the segregated disease list at state 1806. State 1808 is the end of the first loop and returns control to the beginning of the loop at state 1802 once for each disease in the integrated list. Once the first loop has completed, process 1704 advances to state 1810, where a new second loop begins. The second loop cycles through each of the segregated diseases and a decision state 1812 determines if their threshold meets or exceeds the integration threshold. If this value meets or exceeds the integration threshold, the currently processed disease is moved to the integrated disease list by state 1814 effectively reintegrating the disease. Advancing to the end of the second loop at state 1816, control returns to the begin loop state 1810 with the next disease in the list. Once all segregated diseases have been considered, process 1704 ends by moving to return state 1820, and returning control to process 1300.

Figure 19:
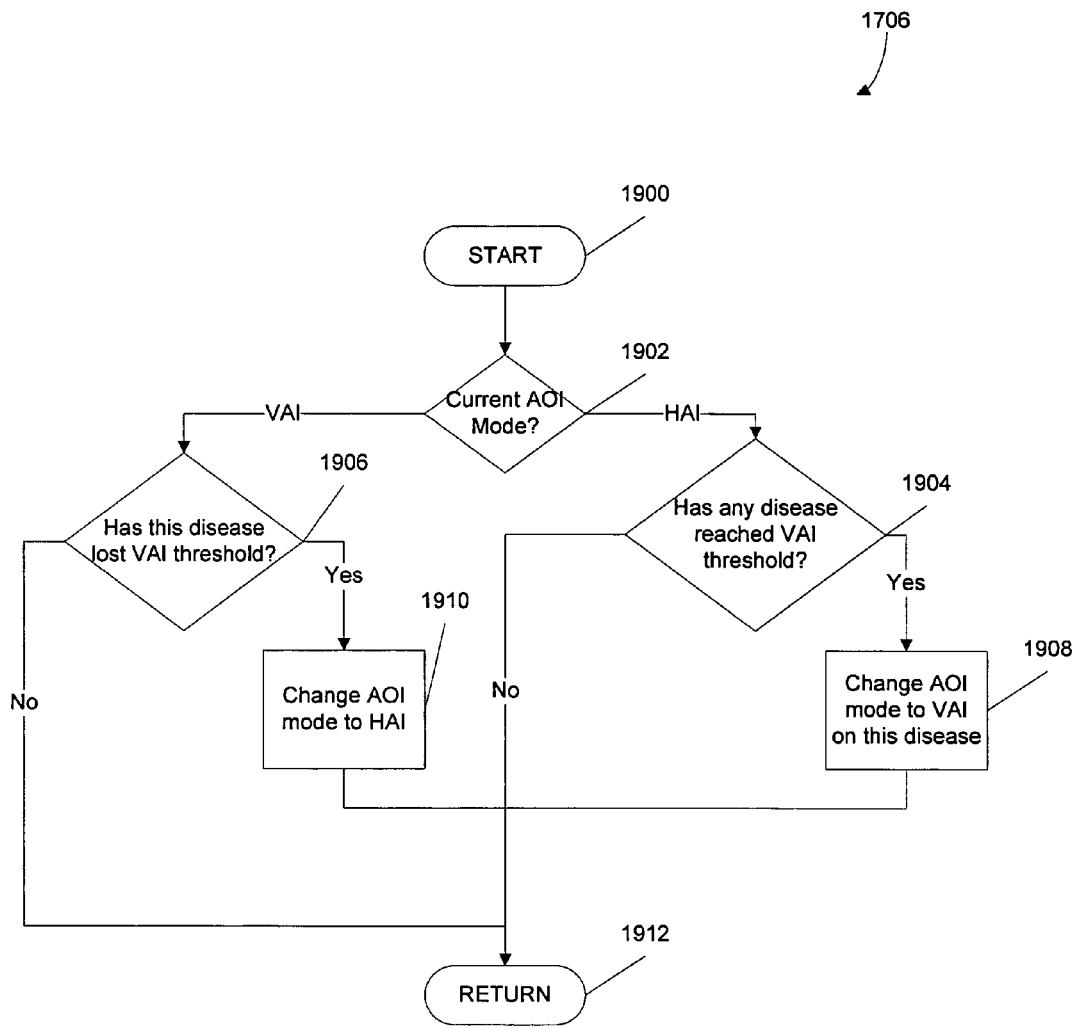
FIG. 19 is an exemplary flowchart of an embodiment of an axis of inquiry process shown in FIG. 17.

Referring again to FIG. 17, control then moves to the AOI sub-system at process 1706. Referring to FIG. 19, process 1706 begins at start state 1900 and moves to a decision state 1902 where the current AOI mode is evaluated. If the system is currently in HAI mode (this is the default mode), process 1706 then advances to a decision state 1904 to determine if any disease has reached its VAI threshold. If any disease is found to reach or exceed its VAI threshold, process 1706 proceeds to state 1908 where the AOI mode is changed to VAI and that disease is selected. Process 1706 then continues to return state 1912 and process 1706 has completed. However; if at decision process 1902, the current AOI mode is VAI, then process 1706 proceeds instead to a decision state 1906 where the current VAI disease is evaluated to determine if it has fallen below its VAI threshold. If so, process 1706 moves to state 1910 where the AOI mode is changed to HAI. However, if decision state 1906 instead determines that the current disease is still at or above its VAI threshold, process 1706 advances to return state 1912, where process 1706 concludes and returns to process 1314 in FIG. 17.

Referring again to FIG. 17, control then advances to a decision state 1708 where the new AOI mode is evaluated. If the AOI mode is VAI, process 1314 moves to HAI process 1710, which is further described in conjunction with FIG. 20 below.

Figure 20:
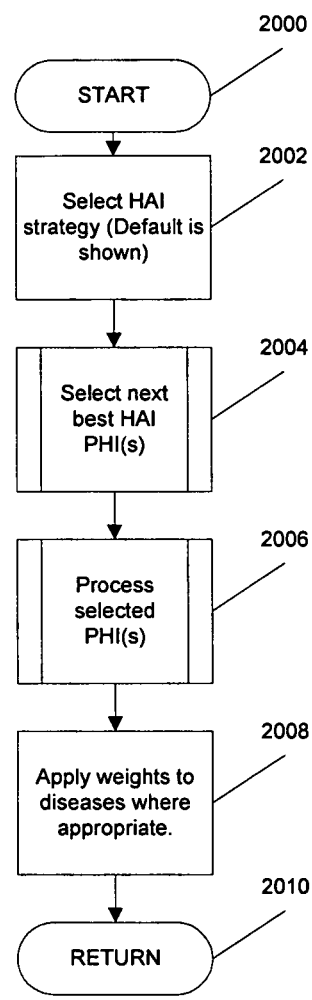
FIG. 20 is an exemplary flowchart of an embodiment of a horizontal axis of inquiry (HAI) process shown in FIG. 17.

Referring to FIG. 20, HAI process 1710 begins at start state 2000 and moves to state 2002 where the HAI strategy is selected by the system. In this case, the default strategy is selected and process 1710 moves to process 2004 where the next best HAI PHI(s) are selected. Other strategies can be used in other embodiments. Process 2004 is further described in conjunction with FIG. 22 below.

Figure 22:
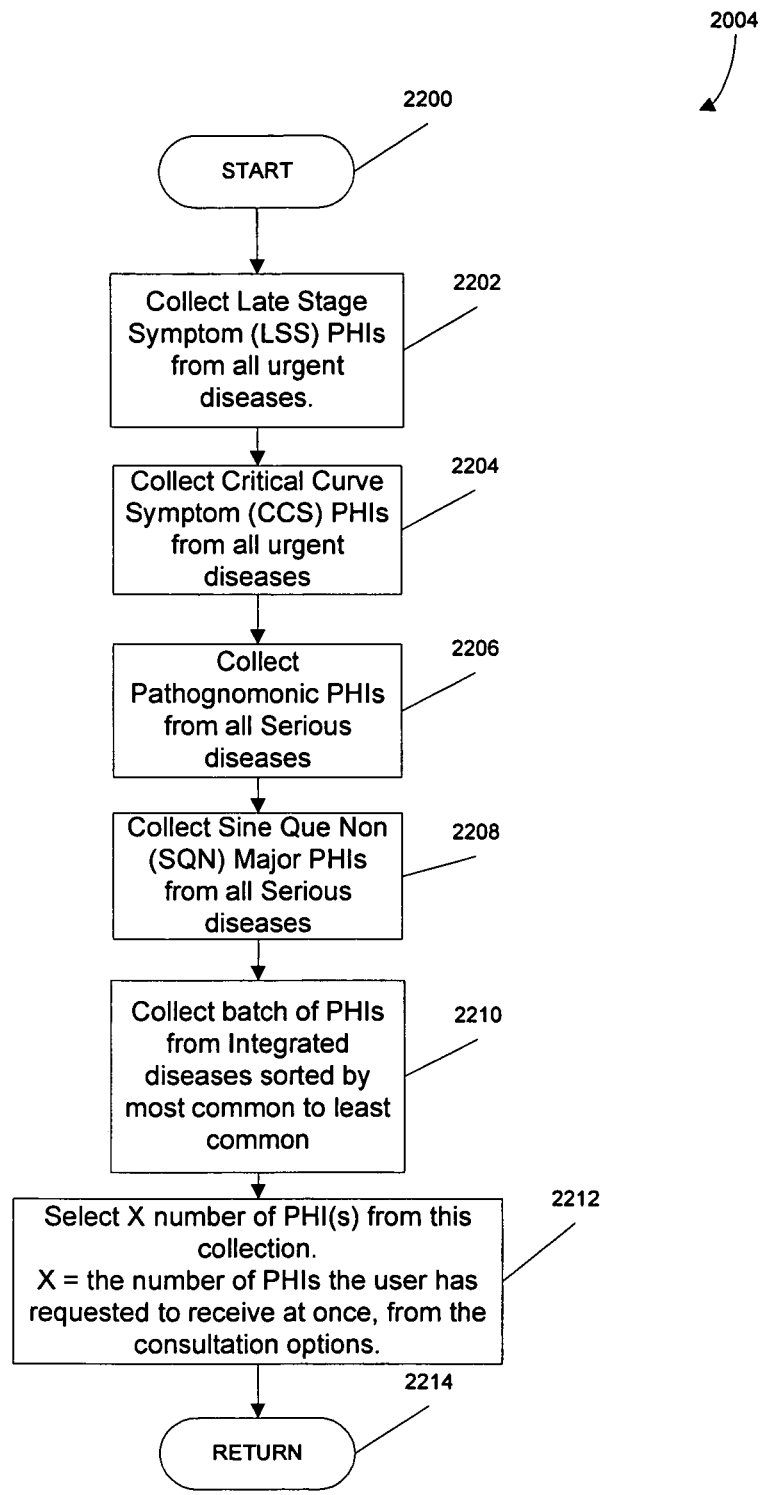
FIG. 22 is an exemplary flowchart of an embodiment of a select next best HAI PHI(s) process shown in FIG. 20.

Referring to FIG. 22, process 2004 begins at start state 2200 and moves to state 2202 where all unanswered LSS (Late Stage Symptoms) are collected from all urgent diseases in the current integrated disease list. Process 2004 then advances to state 2204 where all of the unanswered CCS (Critical Curve Symptoms) PHIs are collected from the urgent diseases in the integrated disease list. Process 2004 proceeds to state 2206 where all of the unanswered pathognomonic PHIs are collected from the serious diseases in the integrated disease list. Process 2004 then advances to state 2208 where all of the unanswered SQN (Sine Que Non) major PHIs are collected from all of the serious diseases in the integrated disease list. Process 2004 then moves to state 2210 where the remaining unanswered PHIs are collected in the order of most common to least common. Process 2004 proceeds to state 2212 where the appropriate number of PHIs, as specified by the consultation options, is taken from the top of the list. Process 2204 then concludes at return state 2214 and returns to HAI process 1710.

Referring again to FIG. 20, process 1710 moves to process 2006 where this list of PHIs is processed. Process 2006 is further described in conjunction with FIG. 23 below.

Figure 23:
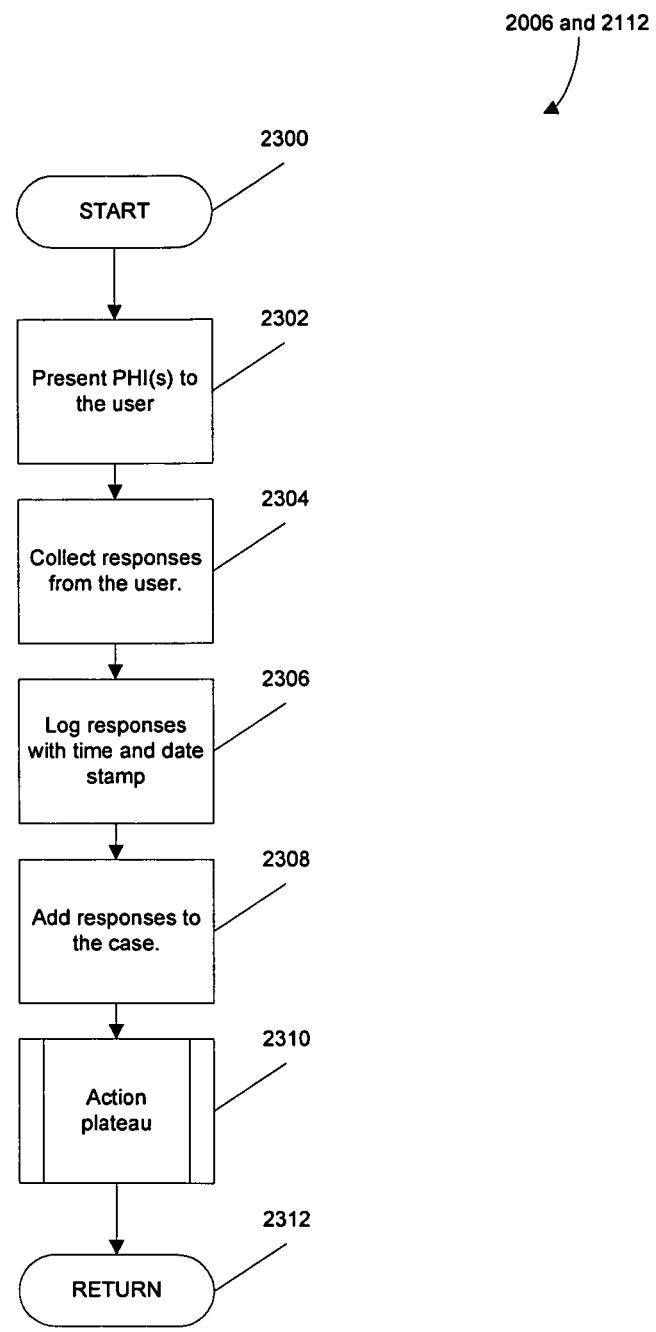
FIG. 23 is an exemplary flowchart of an embodiment of a process selected PHI(s) process shown in FIG. 20 and FIG. 21.

Referring to FIG. 23, process 2006 begins at start state 2300 and moves to state 2302 where the selected PHIs are presented to the user. Process 2006 then moves to state 2304 where the responses from the user are collected for all of the PHIs in the selected PHI list. Process 2006 advances to state 2306 where each PHI, value, and response set is entered into the session log along with a time and date stamp. Process 2006 continues at state 2308 where the PHI, value, and response set are entered into the case. Process 2006 proceeds to action plateau process 2310 where these responses are checked along with all other information collected from the patient to determine if an action plateau has been reached. Process 2310 is further described in conjunction with FIG. 24 below.

Figure 24:
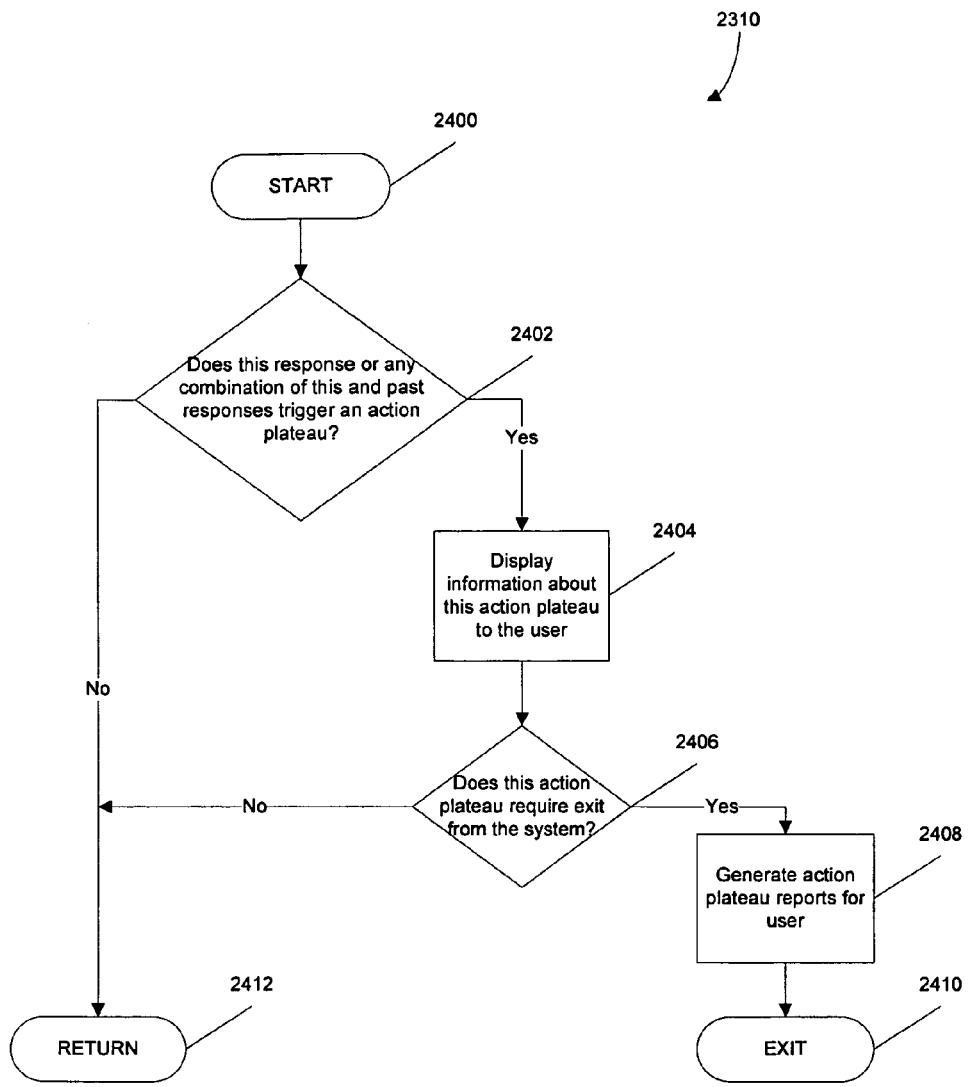
FIG. 24 is an exemplary flowchart of an embodiment of an action plateau process shown in FIG. 23.

Referring to FIG. 24, process 2310 begins at start state 2400 and moves to a decision state 2402 where the user's responses are checked to determine whether or not an action plateau condition has been reached. If an action plateau event has occurred in this case, then process 2310 advances to state 2404. At state 2404, the appropriate advice for this action plateau event is displayed to the user. Process 2310 then proceeds to a decision state 2406 where the action plateau event is evaluated to determine if it warrants an end of this consultation and exit from the system. This type of action plateau is one where it is determined that it might be detrimental or harmful to the patient to stay and finish this consultation. If the current consultation meets these criteria, process 2310 continues to state 2408 where an action plateau report is shown to the patient, in one embodiment. This report may include such things as instructions to dial 911 and activate the local emergency response system, or instructions to call the local poison control center. It may also include information on first aid procedures to perform until help can arrive. At the completion of state 2408, process 2310 proceeds to exit state 2410 where the current user is logged out of the system and the current session is concluded. If, however, the action plateau event did not warrant an exit from the system, as determined at decision state 2406, or if decision state 2402 determined that an action plateau condition was not reached, process 2310 advances to return state 2412 and process 2310 concludes. Control now passes back to process 2006 shown in FIG. 23.

Referring back to FIG. 23, process 2006 advances to return state 2312 where control returns to process 1710 on FIG. 20 and process 2006 is complete.

Referring again to FIG. 20, process 1710 then moves to state 2008 where the weights associated with the PHI, value, and response sets are weighted and these weights are applied to the diagnostic score of all diseases. It is important to note that these weights are applied to all diseases regardless of segregation. In this way, a disease that has been segregated may gain enough diagnostic weight to justify it being reintegrated. Once state 2008 is concluded, process 1710 moves to return state 2010 and control returns to process 1314 on FIG. 17.

Referring back to FIG. 17, process 1314 moves to a decision state 1714 where all of the diseases are checked to determine if they are still capable of reaching diagnostic threshold. If there is no disease that can reach diagnostic threshold even if its remaining PHIs are true, then process 1314 proceeds to state 1718 where the end of consultation flag is set to true and process 1314 is allowed to flow through End loop state 1722 to reach its return state 1724, effectively ending the consultation. If however; there are still more diseases that can reach their diagnostic threshold as determined at decision state 1714, then process 1314 advances to end loop state 1722 and then loops back up to the begin loop state 1702 where the main loop repeats. If, in this or any subsequent iteration of this loop, decision state 1708 finds that the AOI mode has changed to VAI, then process 1314 moves to VAI process 1712.

Figure 21:
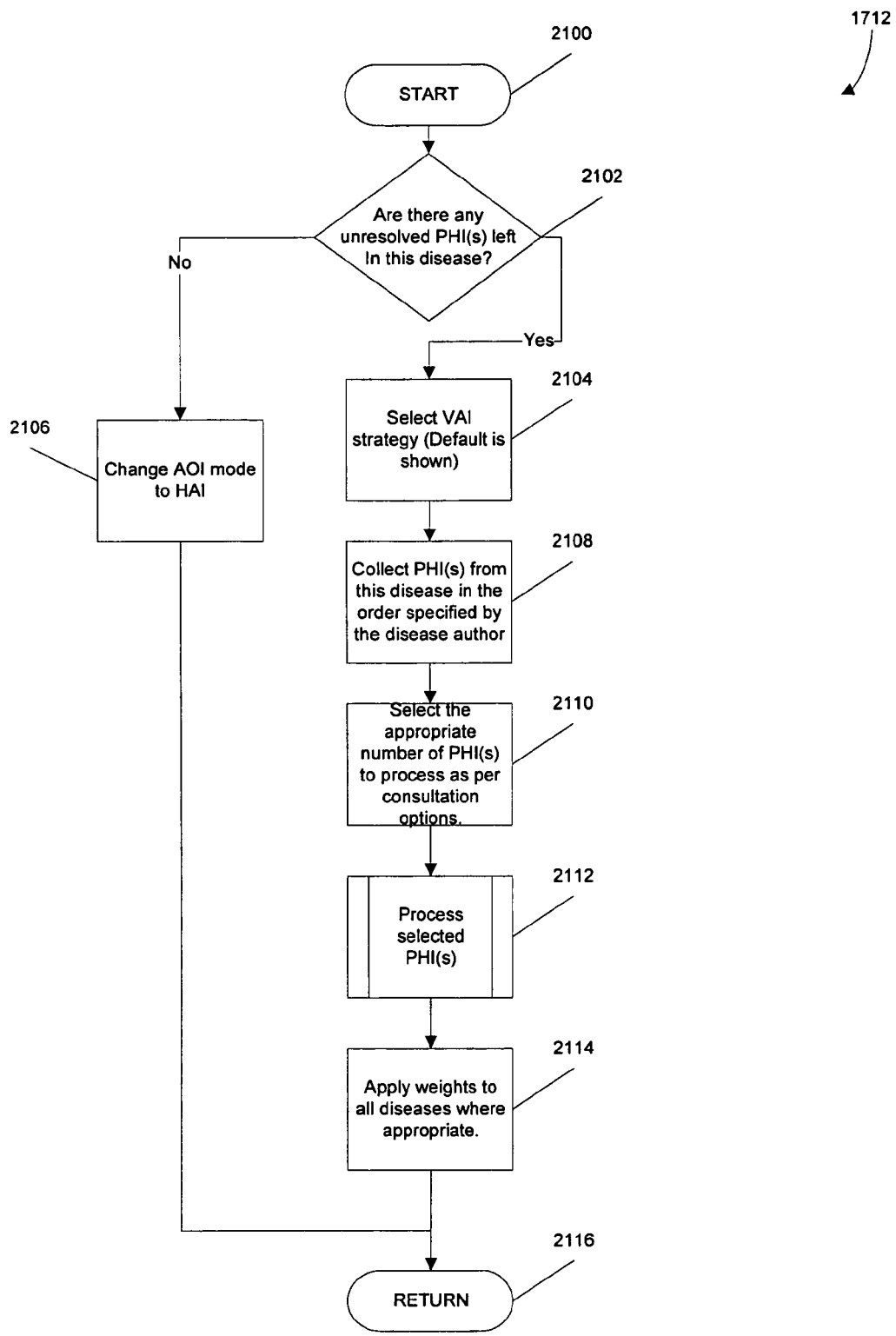
FIG. 21 is an exemplary flowchart of an embodiment of a vertical axis of inquiry (VAI) process shown in FIG. 17.

Referring to FIG. 21, process 1712 begins at start state 2100 and moves to a decision state 2102 where the current disease is checked to determine if it has any unanswered PHIs. If it does not, then no VAI can be performed on this disease and process 1712 advances to state 2106 where the AOI mode is changed back to HAI. Process 1712 then concludes by moving to return state 2116. If, however, decision state 2102 determines that there are unresolved PHIs in this disease, then process 1712 proceeds to state 2104 where the VAI strategy is selected. The default strategy (author specified sequence) is shown in FIG. 21. Other strategies can be used in other embodiments. Process 1712 continues to state 2108 where the unresolved PHIs are collected from the current disease in the order specified by the author of this disease object. Process 1712 advances to state 2110 where the appropriate number of PHIs is selected from the top of this PHI collection according to the preference specified by the user in the consultation options. Process 1712 then moves to process 2112 where the selected PHIs are processed. Process 2112 is the same as process 2006 shown in FIG. 23 and has already been discussed in detail above. Once process 2112 concludes, control returns and process 1712 proceeds to state 2114. Here all diseases are weighted based on the processed PHIs. Process 1712 then concludes by moving to return state 2116 and control returns to process 1314 on FIG. 17.

Referring back to FIG. 17, at the completion of process 1712, process 1314 moves to a decision state 1716. Here the diagnostic threshold of all diseases is checked to determine if they have reached diagnostic threshold. In the event that no disease reaches this threshold, then process 1314 proceeds to end loop state 1722 and the main loop repeats from begin loop state 1702. If, however, a disease does reach its diagnostic threshold, then process 1314 advances to a decision state 1720 and the user is given the option to continue the consultation or to accept this diagnosis. If the user chooses to continue this consultation, then process 1314 moves to end loop state 1722 and the loop repeats from begin loop state 1702. If the user chooses to accept this diagnosis, then process 1314 moves to state 1718, where the end of consultation flag is set to true. This causes process 1314 to flow through the end loop state 1722 and reach its return state 1724. Control is then returned to process 1300 in FIG. 13.

Referring back to FIG. 13, at the completion of process 1314, process 1300 advances to an end consultation process 1316. Process 1316 is further described in conjunction with FIG. 25 below.

Figure 25:
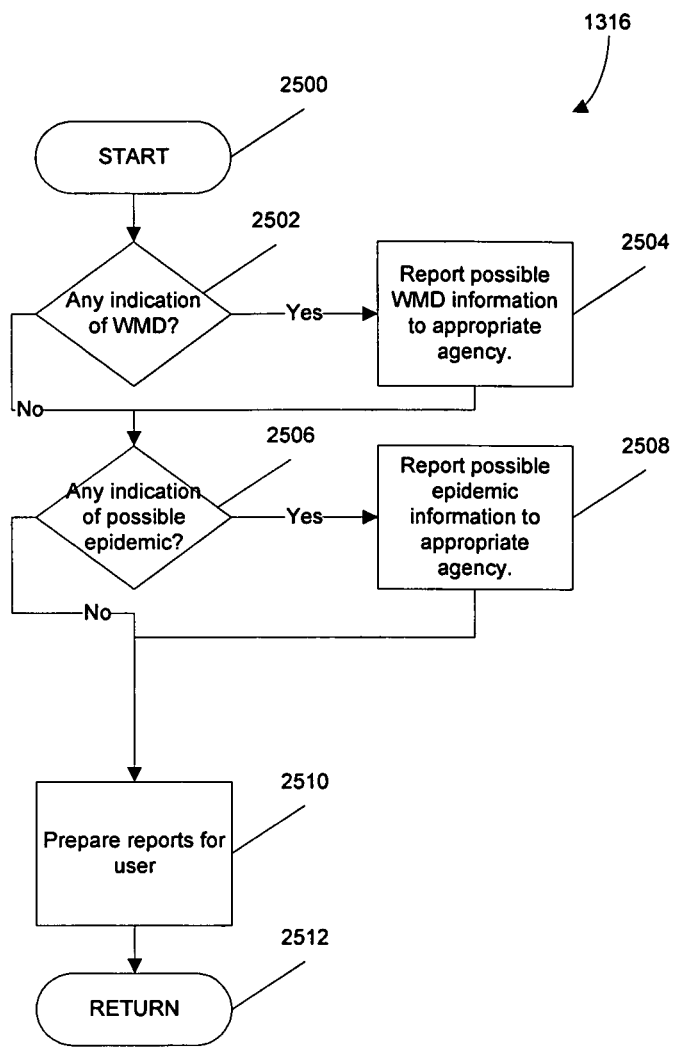
FIG. 25 is an exemplary flowchart of an embodiment of an end consultation process shown in FIG. 13.

Referring to FIG. 25, process 1316 begins at start state 2500 and moves to a decision state 2502 where the consultation is evaluated to determine if any indication of WMD (Weapons of Mass Destruction) is indicated. If any WMD is indicated, then process 1316 moves to state 2504 where a report is sent to the appropriate agency. At the completion of state 2504 or if there are no indications of WMD, process 1316 advances to a decision state 2506. Decision state 2506 determines if there is any indication of a possible epidemic and if so, reports to the appropriate agencies, CDC, etc. at state 2508. At the completion of state 2508 or if there are no indications of a possible epidemic, process 1316 proceeds to state 2510 where all indicated reports are generated for the user. These reports may include a differential diagnosis, requests for followup consultations, medical advice, risk to caregiver reports, and any other reports that are appropriate for this consultation. Process 1316 then concludes by moving to its return state 2512 and control is returned to process 1300 at FIG. 13.

Referring back to FIG. 13, process 1300 is concluded by moving to exit state 1318 where this consultation is closed and the current user is logged out of the system.

Conclusion

Specific blocks, sections, devices, functions, processes and modules may have been set forth. However, a skilled technologist will realize that there are many ways to partition the system, and that there are many parts, components, processes, modules or functions that may be substituted for those listed above.

While the above detailed description has shown, described and pointed out the fundamental novel features of the invention as applied to various embodiments, it will be understood that various omissions and substitutions and changes in the form and details of the system illustrated may be made by those skilled in the art, without departing from the intent of the invention. The foregoing description details certain embodiments of the invention. It will be appreciated, however, that no matter how detailed the foregoing appears, the invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An automated medical diagnostic system, comprising:
   a graphical user interface (GUI) displaying a matrix of cells, each cell being representative of a patient health item (PHI) associated with a particular disease, wherein a first axis of the matrix of cells is organized according to standard anatomic systems and a second axis of the matrix of cells is organized according to different parts of a medical workup; and
   a processor programmed to execute a plurality of diagnostic functions, said processor uses the matrix for input from a user of the GUI, wherein the processor selectively executes the diagnostic functions according to each newly input PHI so as to result in and display a list of possible diagnoses and updated differential diagnosis, wherein:
      one or more cells is representative of a nested matrix of selectable cells, each cell of the nested matrix being representative of at least one disease associated with a subset of the cause of disease acting on an anatomic subsystem of the body;
      when the processor determines that a newly input PHI renders a particular disease impossible to reach a diagnostically significant threshold, the processor removes the particular disease from further consideration in the differential diagnosis and disables the particular disease from suggesting additional PHIs; and
      when the processor determines that a diagnostically significant threshold is reached, the processor segregates any diseases that do not meet or exceed such threshold from suggesting additional PHIs.

2. The system defined in claim 1, wherein the particular disease comprises at least one of one of an abnormality, affliction, ailment, anomaly, disorder, illness, indisposition, infirmity, malady, problem and sickness of a patent.

3. The system defined in claim 1, wherein at least one of the plurality of diagnostic functions comprises computer usable code configured to perform a meta analysis of the input PHIs.

4. The system defined in claim 1, wherein at least one of the plurality of diagnostic functions comprises computer usable code configured to request a user of the system to consult the system at a later time.

5. The system defined in claim 1, wherein a PHI comprises at least one of one of a sign, symptom, complaint, presentation, manifestation, finding, laboratory test result, home test result, and an interpretation of an imaging study.

6. The system defined in claim 1, wherein the GUI is configured for use by a trained health professional.

7. The system defined in claim 1, wherein the processor is configured to provide a differential diagnosis to at least one of veterinarians, chiropractors, dentists, optometrists, and holistic health providers.

8. The system defined in claim 1, wherein the differential diagnosis is a single disease.

9. The system defined in claim 1, wherein the system comprises a handheld computing device, a personal digital assistant (PDA) or a PDA-like computing device.

10. The system defined in claim 1, wherein questions are presented directly to the patient.

11. The system defined in claim 1, in which the processor is configured to automatically recognize potentially dangerous situations and a metric of the potential danger to the patient is graphically displayed by the GUI.

12. The system defined in claim 1, wherein the processor is configured to automatically recognize potentially dangerous situations and a metric of the potential danger to the care giver is graphically displayed by the GUI.

13. An automated medical diagnostic system, comprising:
   a graphical user interface (GUI) displaying a matrix of selectable cells, each cell being representative of at least one disease associated with a cause of disease acting on an anatomic system of the body, wherein a first axis of the matrix of cells is organized according to standard anatomic systems and a second axis of the matrix of cells is organized according to different parts of a medical workup; and
   a processor executing diagnostic software, wherein, in response to selection of a cell via the GUI, the diagnostic software generates a list of possible diagnoses and updates a differential diagnosis associated with the selected cell,
   wherein:
      one or more selectable cells is representative of a nested matrix of selectable cells, each cell of the nested matrix being representative of at least one disease associated with a subset of the cause of disease acting on an anatomic subsystem of the body;
      the diagnostic software is configured to determine that a newly input PHI renders a particular disease impossible to reach a diagnostically significant threshold and remove the particular disease from further consideration in the differential diagnosis; and
      the diagnostic software is configured to determine that a diagnostically significant threshold is reached and segregate any diseases that do not meet or exceed such threshold from populating selectable cells in the nested matrix.

14. The system defined in claim 13, wherein selecting a cell identifies a particular cause of disease and a particular anatomic system of the body and can cause a nested matrix of selectable cells to be displayed, each cell of the nested matrix being representative of at least one disease associated with a subset of the particular cause of disease and a subset of the particular anatomic system of the body.

15. The system defined in claim 13, wherein the anatomic systems of the body include at least one of cardiovascular system, respiratory system, nervous system, digestive system, reproductive system, hematopoietic, ophthalmologic, ear, nose and throat, musculoskeletal, dermatologic, endocrine, whole body, and product of conception.

16. The system defined in claim 13, wherein the causes of disease include at least one of trauma, infection or infestation, allergic or immune, poisoning, environmental, vascular, mental, genetics, nutritional/metabolic/endocrine, oncology, and whole body.

17. The system defined in claim 13, wherein an entire column or entire row of the matrix is selectable.

18. The system defined in claim 13, wherein the diseases represented by the selected cells are unfiltered by previously established patient health items (PHIs).

19. The system defined in claim 13, wherein a single disease is represented by a plurality of cells.

20. The system defined in claim 13, wherein a topographic area of a patient's complaint(s) is indicated on an avatar displayed by the GUI which then causes different diagnostic weights to be added to various diseases.

21. The system defined in claim 20, wherein the topographic area of the avatar is indicated by a patient.

22. The system defined in claim 20, wherein the avatar is used to register the chief complaint of a patient.

\* \* \* \* \*